US010564107B2

(12) United States Patent
Unlu et al.

(10) Patent No.: US 10,564,107 B2
(45) Date of Patent: Feb. 18, 2020

(54) STRUCTURED SUBSTRATES FOR OPTICAL SURFACE PROFILING

(71) Applicant: TRUSTEES OF BOSTON UNIVERSITY, Boston, MA (US)

(72) Inventors: M. Selim Unlu, Jamacia Plain, MA (US); David A. Bergstein, Allston, MA (US); Michael F. Ruane, Hopedale, MA (US); Bennett B. Goldberg, Newton, MA (US)

(73) Assignee: TRUSTEES OF BOSTON UNIVERSITY, Boston, MA (US)

(*) Notice: Subject to any disclaimer, the term of this patent is extended or adjusted under 35 U.S.C. 154(b) by 348 days.

(21) Appl. No.: 15/459,631

(22) Filed: Mar. 15, 2017

(65) Prior Publication Data
US 2017/0234801 A1 Aug. 17, 2017

Related U.S. Application Data

(62) Division of application No. 11/912,565, filed as application No. PCT/US2006/015566 on Apr. 25, 2006, now Pat. No. 9,599,611.

(60) Provisional application No. 60/674,642, filed on Apr. 25, 2005.

(51) Int. Cl.
*G01N 21/77* (2006.01)
*C12Q 1/6816* (2018.01)
*C12Q 1/6837* (2018.01)
*G01N 21/45* (2006.01)
*G01N 21/75* (2006.01)
*G02B 21/34* (2006.01)
*G01N 33/543* (2006.01)
*C12Q 1/6825* (2018.01)

(52) U.S. Cl.
CPC ........... *G01N 21/77* (2013.01); *C12Q 1/6816* (2013.01); *C12Q 1/6825* (2013.01); *C12Q 1/6837* (2013.01); *G01N 21/45* (2013.01); *G01N 21/75* (2013.01); *G01N 33/54373* (2013.01); *G02B 21/34* (2013.01); *B01J 2219/00378* (2013.01); *B01J 2219/00387* (2013.01); *B01J 2219/00432* (2013.01); *B01J 2219/00497* (2013.01); *B01J 2219/00527* (2013.01); *B01J 2219/00576* (2013.01); *B01J 2219/00585* (2013.01); *B01J 2219/00596* (2013.01); *B01J 2219/00605* (2013.01); *B01J 2219/00612* (2013.01); *B01J 2219/00626* (2013.01); *B01J 2219/00637* (2013.01); *B01J 2219/00659* (2013.01); *B01J 2219/00677* (2013.01); *B01J 2219/00707* (2013.01); *B01J 2219/00722* (2013.01); *B01J 2219/00725* (2013.01); *G01N 2021/7779* (2013.01); *G01N 2201/061* (2013.01)

(58) Field of Classification Search
CPC .............................. C12Q 1/6816; G01N 21/77
USPC ............................................................ 506/7
See application file for complete search history.

(56) References Cited

U.S. PATENT DOCUMENTS

| | | |
|---|---|---|
| 5,482,830 A | 1/1996 | Bogart et al. |
| 5,541,057 A | 7/1996 | Bogart et al. |
| 5,644,388 A | 7/1997 | Maekawa et al. |
| 6,346,376 B1 | 2/2002 | Sigrist et al. |
| 6,878,523 B2 | 4/2005 | Nelson et al. |
| 7,110,118 B2 | 9/2006 | Unlu et al. |
| 7,173,256 B2 | 2/2007 | Fox |
| 7,208,322 B2 | 4/2007 | Stolowitz et al. |
| 7,532,314 B1 | 5/2009 | Black et al. |
| 7,695,680 B2 | 4/2010 | Unlu et al. |
| 7,737,392 B2 | 6/2010 | Cunningham et al. |
| 7,742,662 B2 | 6/2010 | Cunningham |
| 7,835,013 B2 | 11/2010 | Jones et al. |
| 7,968,836 B2 | 6/2011 | Cunningham et al. |
| 8,068,995 B2 | 11/2011 | Chau et al. |
| 8,257,936 B2 | 9/2012 | Laing et al. |
| 8,426,028 B2 | 4/2013 | Cai et al. |
| 8,488,120 B2 | 7/2013 | Hall et al. |
| 8,685,755 B2 | 4/2014 | Ferrari et al. |
| 8,830,481 B2 | 9/2014 | Hall et al. |
| 8,841,137 B2 | 9/2014 | DeLouise et al. |
| 8,846,129 B2 | 9/2014 | Lin et al. |
| 8,852,876 B2 | 10/2014 | Fang et al. |
| 8,969,509 B2 | 3/2015 | Liu et al. |
| 9,410,949 B2 | 8/2016 | Singamaneni et al. |
| 9,599,611 B2 | 3/2017 | Unlu et al. |
| 9,638,632 B2 | 5/2017 | Bornhop |
| 9,803,236 B2 | 10/2017 | Zhang et al. |
| 9,862,987 B2 | 1/2018 | Lo et al. |

(Continued)

FOREIGN PATENT DOCUMENTS

| | | |
|---|---|---|
| WO | 2004/083820 A2 | 9/2004 |
| WO | 2009/048494 A1 | 4/2009 |

(Continued)

OTHER PUBLICATIONS

Rao et al. (Biomater Sci., Apr. 1, 2014, 2(4), pp. 436-471) (Year: 2014).*
Matsuura (Feb. 2001) IEEE Journal of Selected Topics in Quantum Electronics vol. 7 pp. 55 to 58.
Emsley (Aug. 2002) IEEE Journal of Selected Topics in Quantum Electronics vol. 8 pp. 948 to 955.
Nikitin (Apr. 20, 2003) Sensors and Actuators B vol. 90 pp. 46 to 51.
Moiseev et al., 2006, DNA conformation on surfaces measured by fluorescence self-interference, Proceedings of the National Academy of Sciences of the United States of America 103:2623-2628.

(Continued)

*Primary Examiner* — Karla A Dines
(74) *Attorney, Agent, or Firm* — Brown Rudnick LLP; Mark S. Leonardo

(57) ABSTRACT

This disclosure provides methods and devices for the label-free detection of target molecules of interest. The principles of the disclosure are particularly applicable to the detection of biological molecules (e.g., DNA, RNA, and protein) using standard $SiO_2$-based microarray technology.

16 Claims, 15 Drawing Sheets

(56) References Cited

U.S. PATENT DOCUMENTS

| | | |
|---|---|---|
| 10,115,013 B2 | 10/2018 | Sibarita |
| 10,151,680 B2 | 12/2018 | Unlu et al. |
| 2003/0112446 A1 | 6/2003 | Miller et al. |
| 2004/0070764 A1 | 4/2004 | Fujimura et al. |
| 2004/0241176 A1 | 12/2004 | Lamparski et al. |
| 2004/0252301 A1 | 12/2004 | Kawano et al. |
| 2005/0130174 A1 | 6/2005 | Bao et al. |
| 2005/0266449 A1 | 12/2005 | Kugler et al. |
| 2006/0014232 A1 | 1/2006 | Inagawa et al. |
| 2006/0063188 A1 | 3/2006 | Zanni et al. |
| 2007/0111224 A1 | 5/2007 | Jung et al. |
| 2007/0278422 A1 | 12/2007 | Einhom et al. |
| 2009/0226031 A1 | 9/2009 | Izuka |
| 2010/0021954 A1 | 1/2010 | Deshayes et al. |
| 2011/0091377 A1 | 4/2011 | Alani et al. |
| 2011/0091384 A1 | 4/2011 | Alani et al. |
| 2012/0036702 A1 | 2/2012 | Einhom et al. |
| 2012/0157350 A1 | 6/2012 | True et al. |
| 2012/0208174 A1 | 8/2012 | Galush et al. |
| 2013/0323756 A1 | 12/2013 | Tullis et al. |
| 2014/0377793 A1 | 12/2014 | Bouamrani et al. |
| 2015/0057949 A1 | 2/2015 | Weinberger et al. |
| 2015/0355133 A1 | 12/2015 | Prasad |
| 2016/0257830 A1 | 9/2016 | Singamaneni et al. |
| 2016/0299069 A1 | 10/2016 | Tao et al. |
| 2016/0334398 A1 | 11/2016 | Weissleder et al. |
| 2016/0375439 A1 | 12/2016 | Li et al. |
| 2017/0016821 A1 | 1/2017 | Unlu et al. |
| 2017/0045451 A1 | 2/2017 | Nolan et al. |
| 2017/0067882 A1 | 3/2017 | Bornhop et al. |
| 2017/0116733 A1 | 4/2017 | Juncker et al. |
| 2017/0234801 A1 | 8/2017 | Unlu et al. |
| 2017/0370709 A1 | 12/2017 | Mace et al. |
| 2018/0031483 A1 | 2/2018 | Singamaneni et al. |
| 2018/0052425 A1 | 2/2018 | Ozcan et al. |
| 2018/0106759 A1 | 4/2018 | de Oliveira Botelho et al. |
| 2018/0120302 A1 | 5/2018 | Bornhop |
| 2018/0148714 A1 | 5/2018 | Hadrup et al. |
| 2018/0275097 A1 | 9/2018 | Sandoghdar et al. |
| 2018/0321231 A1 | 11/2018 | Singamaneni et al. |
| 2018/0364270 A1 | 12/2018 | Chiu et al. |
| 2018/0372678 A1 | 12/2018 | Patolsky et al. |
| 2019/0049440 A1 | 2/2019 | Singamaneni et al. |

FOREIGN PATENT DOCUMENTS

| | | |
|---|---|---|
| WO | 2011/014282 A2 | 2/2011 |
| WO | 2015/031694 A2 | 3/2015 |
| WO | 2015/038205 A1 | 3/2015 |
| WO | 2015/065995 A1 | 5/2015 |
| WO | 2015/085096 A1 | 6/2015 |
| WO | 2015/134847 A1 | 9/2015 |
| WO | 2016/065487 A1 | 5/2016 |
| WO | 2016/164124 A1 | 10/2016 |
| WO | 2017/053516 A1 | 3/2017 |
| WO | 2017/136676 A1 | 8/2017 |
| WO | 2017/196823 A1 | 11/2017 |
| WO | 2018/094200 A1 | 5/2018 |

OTHER PUBLICATIONS

Piehler et al., 1996, Affinity detection of low molecular weight analytes, Analytical Chemistry 68:139-143.

Avci, O. et al., Interferometric Reflectance Imaging Sensor (IRIS)—A Platform Technology for Multiplexed Diagnostics and Digital Detection, Sensors 15(7):17649-17665 (2015).

Carter, E. P. et al., Visualizing Ebolavirus Particles Using Single-Particle Interferometric Reflectance Imaging Sensor (SP-IRIS), Methods in Molecular Biology, 1628:259-270, (2017).

Chan, S. et al., Nanoscale silicon microcavities for biosensing. Materials Science and Engineering C, 15:277-282, (2001).

Collet, J. et al., The elasticity of an individual fibrin fiber in a clot, PNAS, 102(26):9133-9137, (2005).

Cretich et al., Silicon biochips for dual label-free and fluorescence detection: Application to protein microarray development, Biosensors and Bioelectronics, 26(9):3938-3943, (2011).

Cretich, M. et al., Digital detection of biomarkers assisted by nanoparticles: application to diagnostics, Trends in Biotechnology, 33(6):343-351 (2015).

Daaboul, G. G. et al., Digital Sensing and Sizing of Vesicular Stomatitis Virus Pseudotypes in Complex Media; A model for Ebola and Marburg Detection, ACS Nano, 8(6):6047-6055, (2014).

Daaboul, G. G. et al., Enhanced light microscopy visualization of virus particles from Zika virus to filamentous ebolaviruses, PLoS One, 12(6):e0179728:1-15, (2017).

Daaboul, G. G. et al., High-Throughput Detection and Sizing of Individual Low-Index Nanoparticles and Viruses for Pathogen Identification, Nano Letters, 10:4727-4731, (2010).

Daaboul, G. G. et al., LED-Based Interferometric Reflectance Imaging Sensor for quantitative dynamic monitoring of biomolecular interactions, Biosensors and Bioelectronics, 26(5):2221-2227, (2011).

Gagni et al., Combined mass quantitation and phenotyping of intact extracellular vesicles by a microarray platform, Analytica Chimica Acta, 02:160-167, (2015).

Gannavarpu, R. et al., Spatiotemporal Characterization of a Fibrin Clot Using Quantitative Phase Imaging, PLOS ONE, 9(11):e111381:1-7, (2014).

Gong et al., Microparticles in cancer: A review of recent developments and the potential for clinical application, Seminars in Cell & Developmental Biology, 40:35-40, (2014).

Hetagan, A. et al., Visualization of the dynamics of fibrin clot growth 1 molecule at a time by total internal reflection fluorescence microscopy, Blood, 121(8):1455-1458, (2013).

Jamur, MC and Oliver C., Premeabilization of cell membranes, Methods in Molecular Biology, 588:63-66, (2010).

Jenison, R. et al., Interference-based detection of nucleic acid targets on optically coated silicon, Nature Biotechnology, 19:62-65, (2001).

Jorgensen et al., Extracellular Vesicle (EV) Array: microarray capturing of exosomes and other extracellular vesicles for multiplexed phenotyping, Journal of Extracellular Vesicles, 2(1):1-9, (2013).

Lancé, Marcus D., A general review of major global coagulation assays: thrombelastography, thrombin generation test and clot waveform analyasis, Thrombosis Journal, 13:1-6, (2015).

Lu, J. et al., Reflective Interferometric Detection of Label-Free Oligonucleotides, Analytical Chemistry, 76:4416-4420, (2004).

Properzi et al., Exosomes: the future of biomarkers in medicine, Biomarkers in Medicine, 84(3):177-189, (2008).

Rambaran, Roma N. and Serpell, Louise C., Amyloid fibrils, PRION, 2(3):112-117, (2008).

Sandstrom, T. et al., Visual detection of organic monomolecular films by interference colors, Applied Optics, 24:472-479, (1985).

Scherr, S. M. et al., Real-Time Capture and Visualization of Individual Viruses in Complex Media, ACS Nano, 10(2):2827-2833, (2016).

Shao et al., Protein typing of circulating microvesicles allows real-time monitoring of glioblastoma therapy, Nature Medicine, 18(12):1835-1841, (2012).

Su, J. et al., Label-free detection of single nanoparticles and biological molecules using microtoroid optical resonators, Light: Science & Application, 5(1):e16001 (2016).

Thermofisher Scientific, Invitrogen, Alix Plycolonal Anitbiody, retrieved Feb. 25, 2019 [<https://www.thermofisher.com/antibody/product/Alix-Antibody-Polyclonal/PA5-52873>], 4 pages.

Thermofisher Scientific, Invitrogen, Syndecan 4 Polyclonal Antibody, retrieved Feb. 25, 2019 [<https://www.thermofisher.com/antibody/product/Syndecan-4-Antibody-Polyclonal/36/3100>], 5 pages, (2014).

Van Der Pol, E. et al., Optical and non-optical methods for detection and characterization of microparticles and exosomes, Journal of Thrombosis and Haemostatsis, 8(12):2596-2607 (2010).

Vlassov et al., Exosomes: current knowledge of their composition, biological functions, and diagnostic and therapeutic potentials, Biochimica et Biophysica Acta (BBA)—General Subjects, 1820(7):940-948, (2012).

(56) References Cited

OTHER PUBLICATIONS

Wikipedia, Green fluorescent protein, retrieve Feb. 25, 2019, [<https://en.wikipedia.org/wiki/Green_fluorescent_protein>], 19 pages.

Wikipedia, Oligonucleotide, retrieved Feb. 25, 2019, [<https://en.wikipedia.org/wiki/Oligonucleotide>], 4 pages.

Wikipedia, Syntenin-1, 8 pages, retrieved Feb. 25, 2019 [<https://en.wikipedia.org/wiki/Syntenin-1>].

Wikipedia, TSG101, retrieved Feb. 25, 2019, [<https://en.wikipedia.org/wiki/TSG101>], 12 pages.

Yeromonahos, C. et al., Nanostructure of the Fibrin Clot, Biophysical Journal, 99:2018-2027, (2010).

Yurt et al., Single nanoparticle detectors for biological applications, Nanoscale 4(3):715-726, (2012).

Zarovni N., et al., Integrated isolation and quantitative analysis of exosome shuttled proteins and nucleic acids using immunocapture approaches, Methods, 87:46-58 (2015).

Zhu, L. et al., Label-Free Quantitative Detection of Tumor-Derived Exosomes through Surface Plasmon Resonance Imaging, Analytical Chemistry, 86(17):8857-8864 (2014).

\* cited by examiner

STRUCTURED SUBSTRATES FOR OPTICAL SURFACE PROFILING

CROSS-REFERENCE TO RELATED APPLICATIONS

This application is a divisional of U.S. patent application Ser. No. 11/912,565, filed Oct. 25, 2007, which is a 35 U.S.C. § 371 national phase entry of international application PCT/US2006/015566, with international filing date Apr. 25, 2006, which claims the benefit of and priority to U.S. Provisional Patent Application Ser. No. 60/674,642, filed Apr. 25, 2005, the entire contents of each of which are incorporated by reference herein in their entirety.

FIELD OF THE INVENTION

This present invention relates to optical detection systems for biological and other molecules.

BACKGROUND OF THE INVENTION

Fields as diverse as bioresearch, ecology, medicine, pharmacology, drug discovery and biohazard detection have a critical need for large-scale biomolecule affinity sensing. Affinity sensing detects the presence and/or affinity of "target" biomolecules using other "capture" biomolecules. Target molecules include DNA segments, RNA segments, protein, and small molecules and the capture molecules are often derivatives of their natural (i.e., in vivo) binding partners which are also typically DNA, RNA, and protein, but may also include small molecules having a high binding affinity. Microarray detection systems are a technology that has the potential to assess large numbers of target molecules in a relatively rapid manner, making it a useful high-throughput methodology (FIG. 1). From tens to more than a million different capturing agents are fixed in localized spots or features on the microarray substrate (e.g., glass). Typically, target molecules are obtained from a biological or environmental sample, purified, and fluorescently labeled with a dye molecule including but not limited to Cy5, Cy3, quantum dots, or biotin for subsequent labeling with streptavidin or antibodies. The prepared sample is exposed to the array. The array is then rinsed and placed in a fluorescent scanner that measures the fluorescent signal from every target molecule location.

Throughput refers to the number of target molecule spots measured in a single experiment. Each spot measures the affinity for molecules in the sample for the fixed capturing agent attached to the substrate at that position. High throughput methods are advantageous because they allow the simultaneous detection of a large number of target molecules in a single experiment.

Microarrays are actively being used today in biological research and their use is expected to expand over the next decade in the areas of medical diagnosis, drug discovery, and bio-weapons detection. Currently, DNA microarrays observing DNA-DNA interaction constitute the vast majority of microarray use, although the technology for protein-protein and protein-DNA arrays is rapidly advancing.

Despite widespread use, microarrays have their limitations. Specifically, the target molecules must be fluorescently labeled for detection. The labeling may add ambiguity and, in certain instances, precludes microarrays from many applications where affixing a label to the target molecules may not be practical or possible. Proteins, for instance, pose a particularly significant labeling challenge because attachment of a fluorescent label is likely to alter the conformation and hence the binding properties of the protein. Even DNA labeling, the most widely used and reliable microarray assay, can be unreliable because (i) the label may affect the DNA binding properties, (ii) the labeling procedure may be time consuming and costly, (iii) each DNA molecule may receive zero, one, or more than one label reducing the statistical significance of the measured result, (iv) labels may non-specifically bind to the background and cloud the signal, and/or (v) background auto-fluorescence from the substrate may cloud the fluorescent label signal. Thus, a label-free detection technology for microarray assays is preferable.

There are a number of optical label-free technologies currently under development including waveguides [Lukosz 1990], surface plasmon resonance [Brockman 2000], optical gratings [Lin 2002], and cantilevers [Zhang 2004]. None of which these technologies have yet demonstrated significant throughput. Surface plasmon resonance (SPR), for example, is available with the capability of 400 simultaneous observation sites. SPR requires the use of a metallic surface which precludes the well-established and accepted microarray chemistries developed for $SiO_2$. Also, SPR does have the benefit of detecting binding events in real-time which enables the observer to gather kinetics information about the binding reactions. Likewise, however, standard fluorescent microarrays demand dry samples which also precludes obtaining real-time kinetics information. Thus, SPR and standard fluorescent-based microarray assays are satisfactory only for those applications in which throughput is more critical than kinetics information. There is a need for a system that may be used either for real-time measurements for kinetics information, or as a dried assay to collect only binding data.

Optical surface profilers are devices that detect small height changes across a surface using optical interference measurements. Optical surface profilers are used in many semiconductor processing labs and work by one of two principles: phase shift interferometry (PSI) or white light interferometry (WLI) (FIG. 2). PSI works by illuminating a reflecting sample with single wavelength light. The illumination beam is split so that part reflects off the sample and part reflects off a reference surface before they are recombined and imaged on a camera. The beams interfere when combined to form an interference pattern also known as an interferogram which is imaged and recorded by a camera (e.g., a CCD camera). The reference mirror position is scanned to create different path lengths for the reflected beam while the interferogram at each position is captured by the camera. When the path length between the reference reflector position and the sample surface position at a particular location is the same, or off by an integer multiple of the wavelength, the intensity at that pixel is maximum. This indicates the relative surface height at that position. This PSI method works well when the measuring relative heights shorter than the one half of the wavelength ($\lambda/2$) to avoid ambiguity in the relative measurement.

WLI is an alternative optical profiling technique that avoids the ambiguity inherent in PSI. The WLI setup and measurement procedure is essentially the same as for PSI (i.e., the light is split with part going to the sample, part going to a reference reflector, and the reflections are combined and images onto a camera). The difference between the techniques is that instead of using a single wavelength (PSI), a spectrally broad illumination source is used. With a spectrally broad source, the two combined beams will only interfere constructively when the path length for either reflection is the same without the integer multiple of the wavelength caveat of the PSI method. These existing optical profiling methods in the semiconductor field, however, lack sensitivity for biosensing applications where low-index biomaterial is binding to a low-index glass surface.

Optical interferometric methods have been more recently developed specifically for biosensing applications [Pichler 1996; Moiseev 2006]. One such method is spectral interference (SI). The sample used in SI consists of target molecules on a semitransparent layer. Light reflecting from both the top and bottom surfaces of the semitransparent layer with the biomaterial interferes in the reflected beam (FIG. 3). The spectrum of the combined reflections from the top and bottom layer interface is used to determine the layer thickness and hence molecule binding to the substrate surface. Some wavelengths will experience constructive interference while other wavelengths will experience destructive interference based on the thickness of the semitransparent layer. There are two primary reflections, one from the top surface and one from the bottom surface with less significant higher order reflections that make multiple passes through the semitransparent layer and contribute less to the signal. While these secondary reflections contribute less, they do improve the measurement by helping distinguish the wavelengths experiencing constructive interference from wavelengths experiencing destructive interference. The combined reflected beam is measured by a spectrometer. Wavelengths where the interference is destructive are attenuated. The spectrum is used to determine at which wavelengths the interference is destructive and constructive, and hence the apparent thickness of the semitransparent layer, for which bound biomaterial increases the apparent thickness. Thus, knowing the initial thickness of the semitransparent layer allows a calculation of the height of the biomaterial on the surface. The disadvantage of this method for use as a biosensor is that the method is performed by a spectrometer and can be applied to only one location at a time. It is difficult to measure the spectrum of spectrally broad light at many nearby locations simultaneously, meaning that the technique is not useful for the high resolution imaging necessary to read modern microarrays.

The present invention solves many of the problems of the prior art, including providing a real-time, label-free microarray system suitable for high throughput screening. Additionally, the invention may be adapted to take advantage of the well-established chemistry developed for attaching capture molecules to $SiO_2$-based microarray substrates.

SUMMARY OF THE INVENTION

The present invention provides methods and devices for the label-free detection of target molecules of interest. The principles of the disclosure are particularly applicable, but not limited to the detection of biological target molecules (e.g., DNA, RNA, protein, small molecules, and environmental contaminants) using standard $SiO_2$-based microarray technology.

In one aspect, the invention provides a layered substrate comprising a base layer, at least one, coating layer having a refractive index different from that of the base layer, and a plurality of spatially distinct binding locations, wherein each of the binding locations comprises capture molecules bound to the topmost coating layer. Desirably, the base layer has a high refractive index. In other embodiments, the at least one coating layer has an index between about 1.1 and about 1.7 (e.g., about 1.4). Particularly useful base layers comprise silicon and particularly useful coating layers comprise $SiO_2$, Si3N4, and gold. In other desirably embodiments, the layered substrate comprises at least two different coating layers. Optionally, the layered substrate is constructed having a plurality of reaction wells. Further, each well may be considered a binding location.

Desirably, each of the binding locations comprise a single type of capture molecule and capture molecules are preferably DNA, RNA, protein, or small molecules having high affinity and specificity for a target molecule of interest. In useful embodiments, the capture molecules are covalently bound to the topmost coating layer. Particularly useful layered substrates comprise a base layer of Si and a coating layer of $SiO_2$, wherein the coating layer has a thickness of between about 150 nm and about 20 microns, but preferably between about 1 micron and about 20 microns or between about 150 nm and about 500 nm.

In another aspect, the invention provides an optical detection apparatus comprising:
(i) a tunable light source, wherein the light source produces substantially collimated light characterized by an illumination wavelength;
(ii) a reflective substrate comprising capture molecules bound to the uppermost surface; and
(iii) a photodetector array operably linked to a central processor capable of measuring the intensity of the light reflected from the substrate.

In some embodiments, the light source is a tunable laser or a broad spectrum light source operably linked to a tunable filter. In other embodiments, the substrate is a layered substrate constructed in accordance with the principles of this disclosure. Useful photodetector arrays include a CCD camera and an InGaAs array. Desirably, the light source is tunable over a wavelength range of at least 5 nm, 15 nm, 50 nm, or more. Useful wavelength ranges include, for example, wavelengths within the range of about 1450 nm to about 1650 nm. Desirably, the central processor is capable of calculating reflectivity curves of illumination intensity as a function of illumination wavelength for substantially every pixel of said photodetector array.

In another aspect, the invention provides an optical detection apparatus comprising:
(i) a light source capable of producing an illumination beam, wherein the illumination beam is substantially collimated;
(ii) a reflective substrate comprising capture molecules bound to the uppermost surface;
(iii) a reference reflector having substantially the same refractive index as the reflective substrate;
(iv) a first beam splitter capable of splitting the illumination beam into a sample illumination beam and a reference illumination beam, the beam splitter further capable of directing said sample illumination beam onto a reflective substrate and directing the reference illumination beam onto a reference reflector;
(v) a second beam splitter capable of combining the light reflected from the reflective substrate with the light reflected from the reference reflector into an imaged light beam;
(vi) a means for displacing the reference reflector in a direction of the reference illumination beam; and
(vii) a photodetector array positioned to measure the intensity of the imaged light beam operably linked to a central processor capable of capturing images produced by the photodetector array.

The illumination beam contains either substantially a single wavelength (e.g., generated by a single wavelength laser and a broad spectrum light source operably linked to a narrow bandpass filter) or multiple wavelengths (e.g., white light). In other embodiments, the substrate is a layered substrate constructed in accordance with the principles of this disclosure. Useful photodetector arrays include a CCD camera and an InGaAs array. Desirably, the light source is tunable over a wavelength range of at least 5 nm, 15 nm, 50 nm, or more. Useful wavelength ranges include, for example, wavelengths the range of about 1450 nm to about 1650 nm. In one embodiment, the first beam splitter and the second beam splitter are combined in a single element. Desirably, the central processor is capable of calculating reflectivity curves of illumination intensity as a function of the displacement position of said reference reflector for substantially every pixel of said photodetector array.

In another aspect, the invention provides a method for measuring target molecule binding to a microarray, the method comprising:
(i) providing a microarray comprising a plurality of spatially distinct binding locations, wherein each binding location comprises substantially a single type of capture molecule bound to the surface of said microarray and each type said capture molecules specifically bind a type of target molecule;
(ii) contacting the microarray with a sample comprising one or more target molecules;
(iii) assessing the binding of said target molecules to said capture molecules by:
(a) sequentially illuminating the microarray with varying wavelengths using a tunable light source;
(b) measuring the intensity of the light reflected of the microarray at each of the illuminating wavelengths using a photodetector array;
(c) calculating the substrate reflectivity as a function of illuminating wavelength for each pixel of the photodetector array; and
(d) comparing the calculated function to the function calculated prior to the contacting step (ii), wherein a difference in the function at a pixel is an index of the binding of the target molecules to the capture molecules.

Optionally, the microarray comprises a layered substrate constructed in accordance with the principles of this disclosure. Useful capture molecules include, for example, DNA, RNA, protein, and small molecules and are preferably covalently bound to the uppermost surface of the microarray. The target molecules may be present in any type of sample, but particularly useful samples include biological and environmental samples. Useful photodetector arrays include a CCD camera and an InGaAs array. Desirably, the tunable light source is tunable over a wavelength range of at least 5 nm, 15 nm, 50 nm, or more. Useful wavelength ranges include, for example, wavelengths the range of about 1450 nm to about 1650 nm.

In useful embodiments, the comparing step (d) comprises assessing either the difference or the ratio between the function and the function prior to the contacting step (ii).

The foregoing method may also be adapted for use wherein the microarray is present within a flow cell and the assessing step (iii) is repeated at least three times. In this case, it is desirable that the assessing step (iii) is performed at least once prior to binding equilibrium between at least one of the target molecules and one of the capture molecules.

In another aspect, the invention provides a method for measuring target molecule binding to a microarray, the method comprising:
(i) providing a microarray comprising a plurality of spatially distinct binding locations, wherein each binding location comprises substantially a single type of capture molecule bound to the surface of said microarray and each type the capture molecules specifically bind a type of target molecule;
(ii) contacting the microarray with a sample comprising one or more target molecules;
(iii) assessing the binding of the target molecules to the capture molecules by:
(a) providing an illumination beam;
(b) splitting the illumination beam into a sample illumination beam that is directed onto said microarray, and a reference illumination beam that is directed onto a reference reflector;
(c) combining the light reflected from said microarray with the light reflected from the reference reflector into a reflected beam;
(d) measuring the intensity of the reflected beam using a photodetector array;
(e) repeating steps (b)-(d) for a plurality of reference reflector positions;
(f) calculating the reflected beam illumination intensity as a function of the reference reflector position for each pixel of the photodetector array; and
(g) comparing the calculated function to the function calculated prior to the contacting step (ii), wherein a difference in the function at a pixel is an index of the binding of the target molecules to the capture molecules.

Optionally, the microarray comprises a layered substrate constructed in accordance with the principles of this disclosure. Useful capture molecules include, for example, DNA, RNA, protein, and small molecules and are preferably covalently bound to the uppermost surface of the microarray. The target molecules may be present in any type of sample, but particularly useful samples include biological and environmental samples. Useful photodetector arrays include a CCD camera an InGaAs array. The illumination beam is substantially a single wavelength (e.g., generated either by a single wavelength laser or a broad spectrum light source operably linked to a narrow bandpass filter). Alternatively, the illumination beam comprises multiple wavelengths (e.g., white light). Useful wavelength ranges for the illumination beam include, for example, wavelengths the range of about 1450 nm to about 1650 nm.

In useful embodiments, the comparing step (g) comprises assessing either the difference or the ratio between the function and the function prior to the contacting step (ii).

The foregoing method may also be adapted for use wherein the microarray is present within a flow cell and the assessing step (iii) is repeated at least three times. In this case, it is desirable that the assessing step (iii) is performed at least once prior to binding equilibrium between at least one of the target molecules and one of the capture molecules.

BRIEF DESCRIPTION OF DRAWINGS

The foregoing and other features and advantages of the present disclosure will be more fully understood from the following detailed description of the exemplary embodiments, taken in conjunction with the accompanying drawings in which:

FIG. 11A is a graph showing the measured reflective intensity as a function of wavelength for pixels corresponding to physical locations having a height difference of 10 nm; FIG. 11B is a 3D mesh graph of the surface of a test substrate; FIG. 11C is a 2D image of pixel intensity showing the apparent pixel height corresponding to the surface of a test substrate;

DETAILED DESCRIPTION

The present invention provides devices and methods for optically profiling the height of a substrate. These techniques are applied to the detection of target molecules bound to the surface of microarrays. Significant advantages over prior art methods include, but are not limited to, the label-free detection of biological and environmental target molecules in a microarray-style assay (i.e., using capture molecules to immobilize the target molecules) that allows for high throughput screening. Further, the invention may be adapted to provide real-time binding information in order that binding kinetics of individual target-capture molecule interactions may be determined.

Three interferometry methodologies consistent with the principles of this invention are described. In each case, the highly sensitive detection to small height changes of a low-index binding surface is enabled by one or more semitransparent layers below the binding surface. When adapted to microarray detection, the low-index binding material consists of the low-index substrate with immobilized capture molecules on the surface. Captured target molecules (i.e., the molecules of interest) causes an increase in the apparent height of the binding surface, where the height change is an indicator of the amount of target molecules bound to the surface.

A. Direct Reflectivity Method

The direct reflectivity method is the primary substrate enhanced method for the label-free detection of microarray binding. As described in more detail below, the basic principle of the invention uses a top illumination source bright field microscope which is reflected from the surface into a photodetector array (e.g., a CCD camera). The image that is formed is essentially an image of the reflectivity of the sample at every point. It would be difficult to detect molecules binding to the microarray surface fabricated on standard glass and using a normal microscope and collimated illumination source because the reflectivity change resulting from target molecule binding would be too small to reliably quantify.

Figure 1:
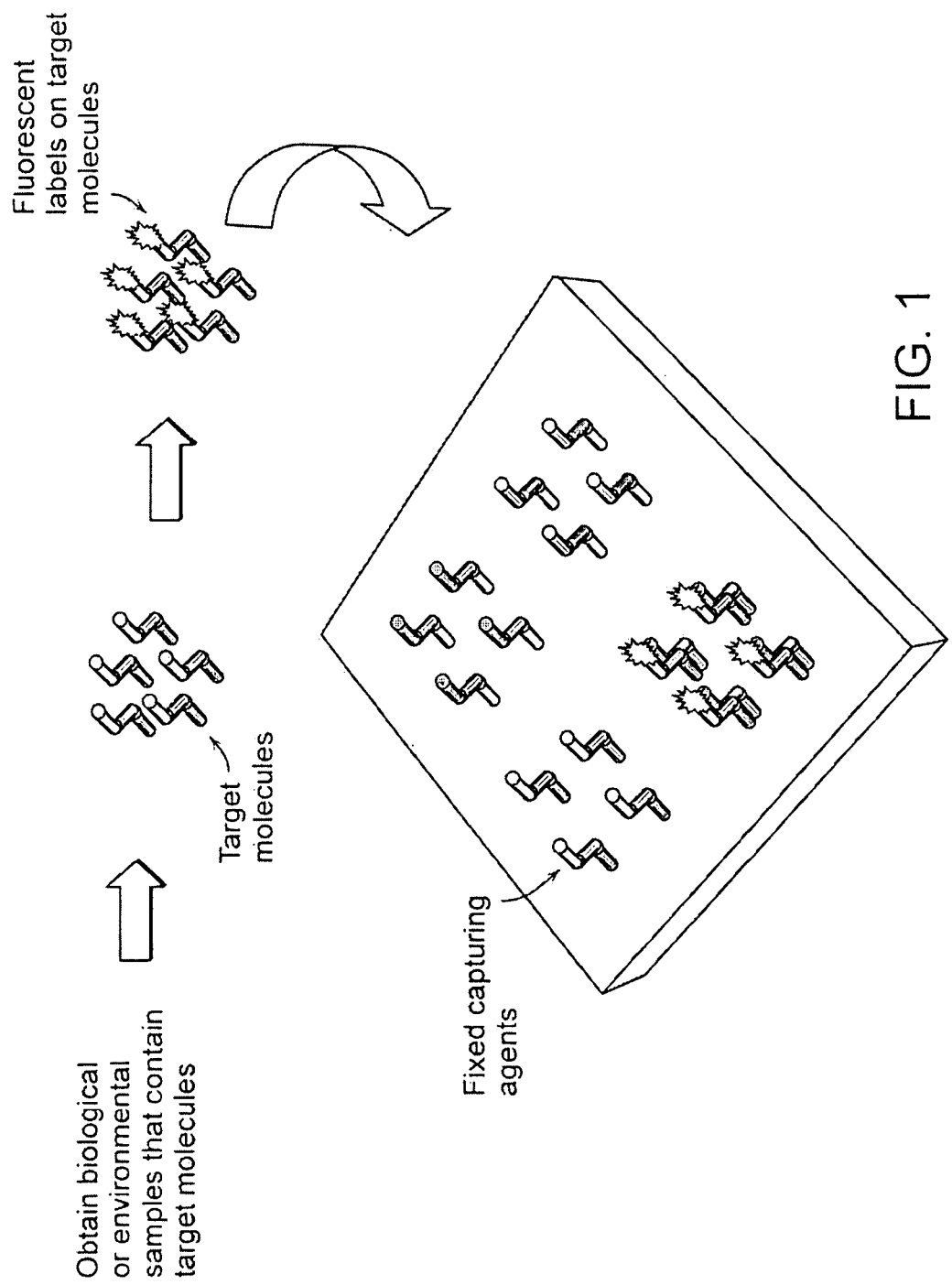
FIG. 1 is schematic of a microarray methodology using fluorescence detection.
Figure 2:
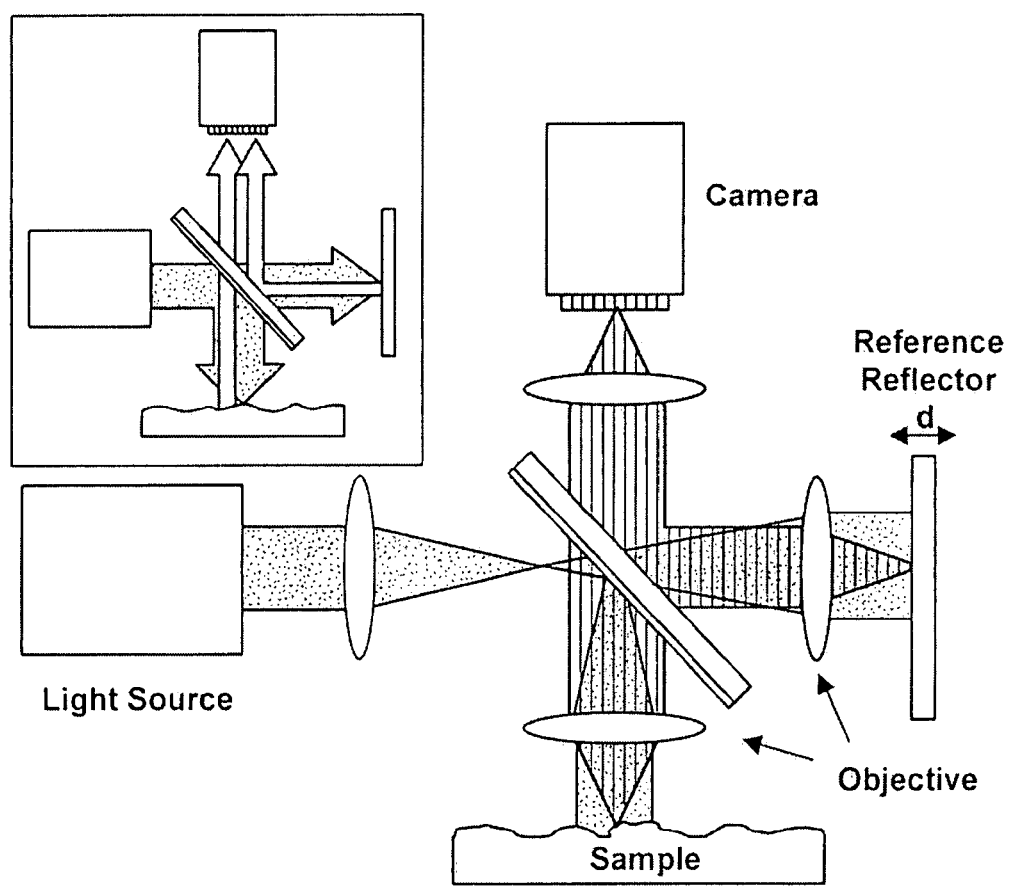
FIG. 2 is a schematic diagram for a device capable of performing phase shift interferometry (PSI) or white light interferometry (WLI)
Figure 3:
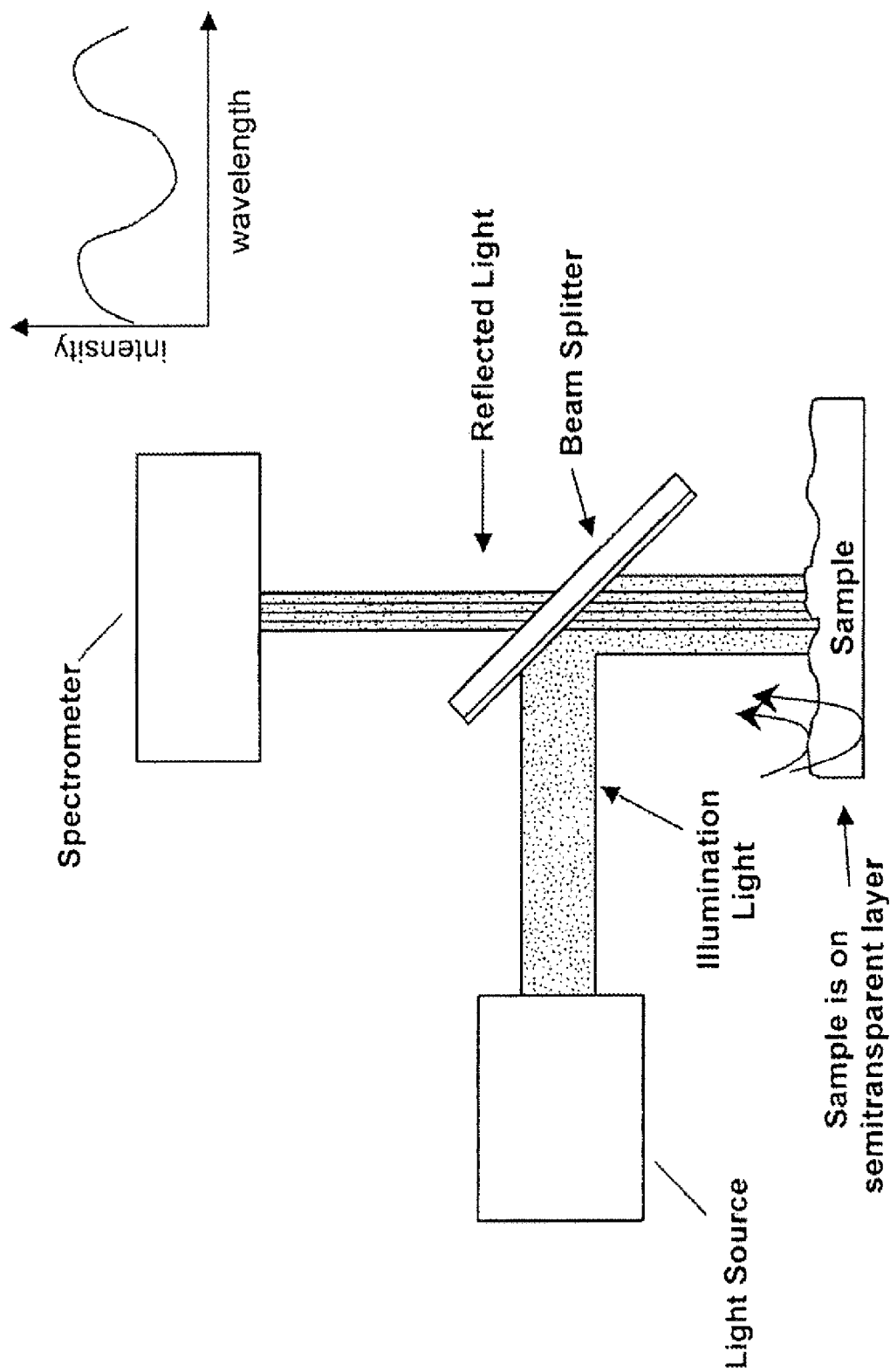
FIG. 3 is schematic diagram for a device capable of measuring spectral interference (SI); the inset is a hypothetical interference spectrum that could be obtained using SI.
Figure 4A:
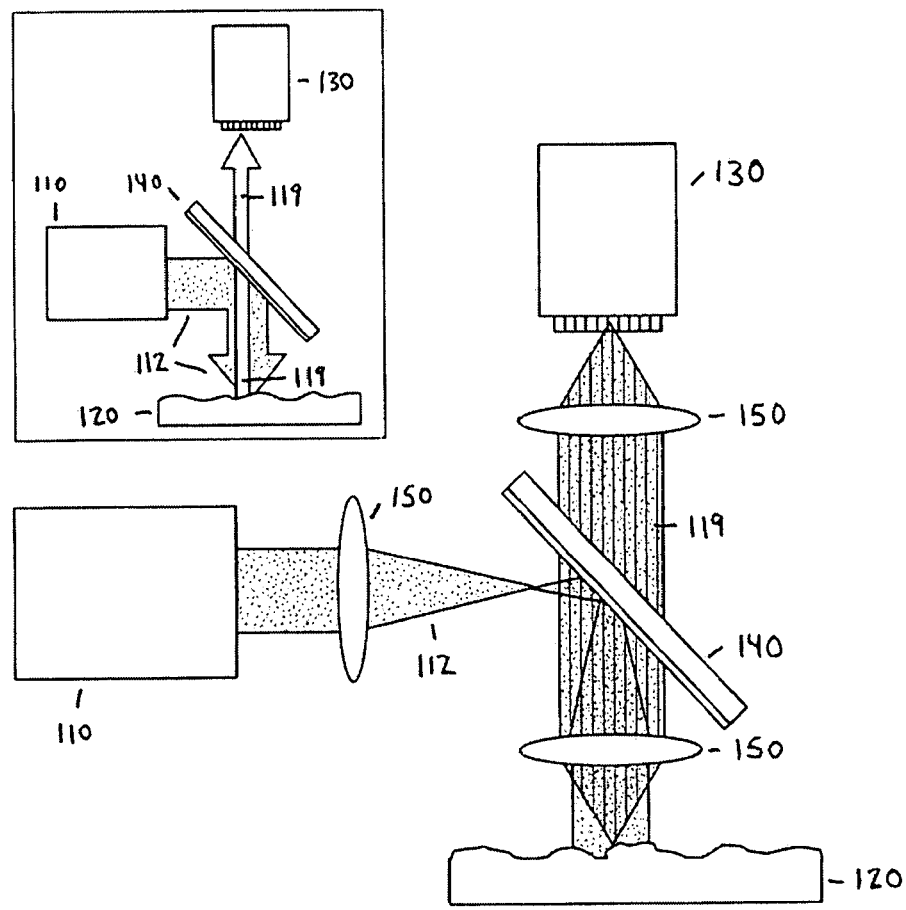
FIG. 4A is schematic diagram of the direct reflectivity methodology; the inset is a simplified schematic showing the light paths.
Figure 4B:
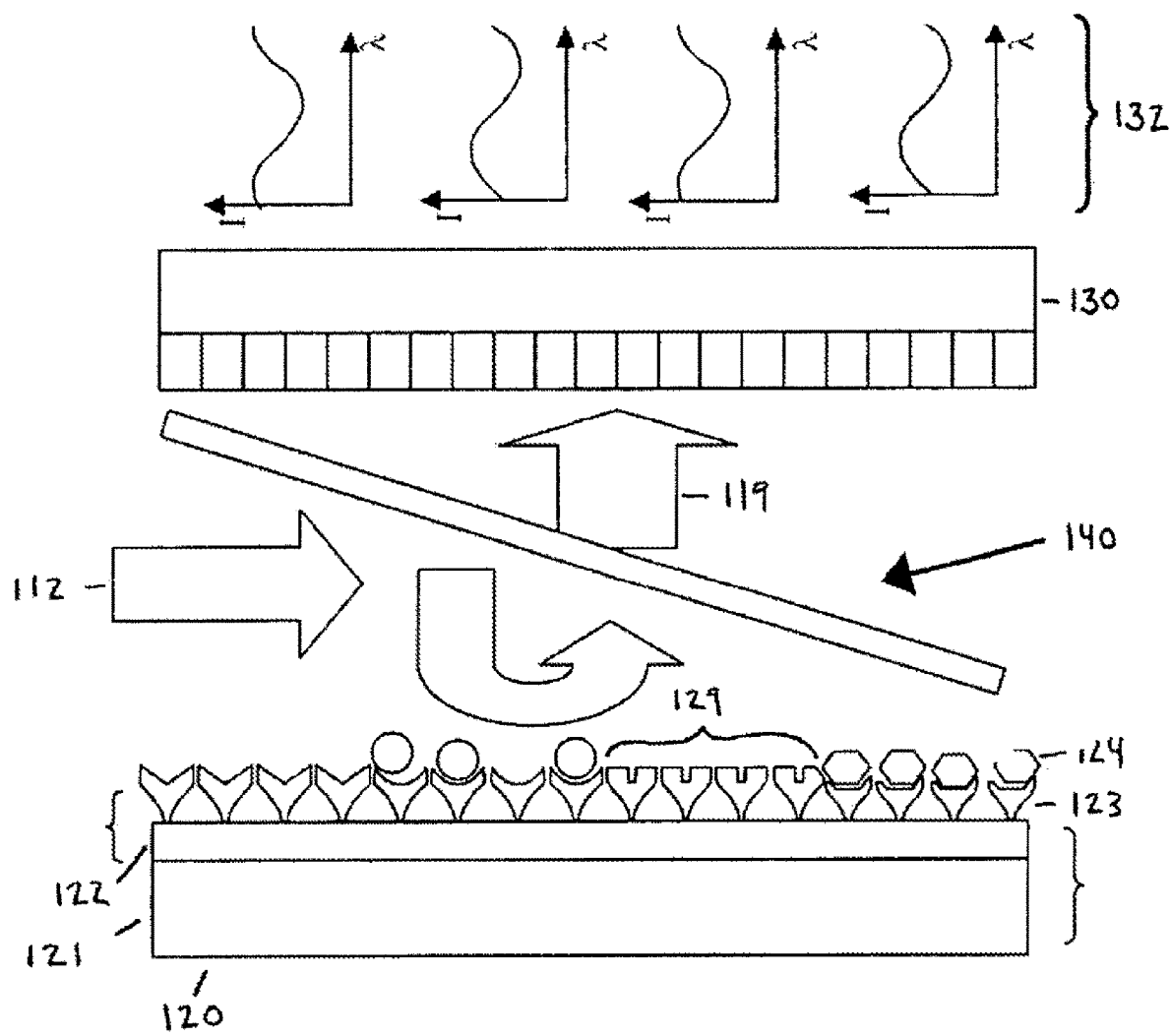
FIG. 4B is a schematic diagram showing features the layered substrate (e.g., microarray) and parts of the direct reflectivity methodology.

Several modifications must be made to the standard microscope and microarray set-up in order to obtain significant and observable changes in reflectivity caused by target molecule binding. FIG. 4A and 4B are schematic illustrations of one such set-up that illustrates the principles of the direct reflectivity method. The illumination source 110 is a tunable laser and an appropriate photodetector array 130 (camera) is selected based on the laser's wavelength range. The illumination beam 112 is directed from above onto a layered microarray 120, preferably perpendicular to the plane of the microarray 120. Optionally, the illumination beam 112 is directed onto the microarray 120 using a beam splitter 140. The imaged light 114 is reflected from the microarray 120 onto the photodetector 130 where an image is captured. Optionally, objectives 150 are used to focus the illumination beam 112 and/or the imaged light 119. Desirably, all optical components are coated with an anti-reflective coating appropriate for the wavelength range used. The microarray 120 is fabricated as a layered substrate consisting of a thick, reflective lower substrate (base layer 121) and a thin coating of a low index material (coating layer 122). For example, one particularly useful microarray substrate has 10 microns of $SiO_2$ layered on a 300 micron thick Si wafer. FIG. 4B shows a simplified schematic diagram of the principles of this embodiment. The microarray 120 is formatted as a plurality of spatially distinct locations 129. The locations 129 may have the same or different target molecule 124 binding specificities compared to each other location 129 on the microarray 120. Each location 129 contains a plurality of substantially identical capture molecules 123 that specifically bind a single type of target molecule 123. To measure target molecule 124 binding to the surface of the microarray 120, the laser 110 wavelength is then swept through its tuning range and the reflectivity from each position on the microarray 120 is recorded as a function of position and wavelength, resulting in a reflectivity vs. wavelength curve. As target molecules 124 bind to the capture molecules 123 on the microarray 120 surface, the reflectivity vs. wavelength curve 132 for each point of the surface will change in an observable way compared to the unbound state.

In one example of the direct reflectivity method, the tunable laser illumination source 110 has a range of 1500 nm to 1580 nm. The photodetector array 130 is an InGaAs array based camera appropriate for these wavelengths. The layered microarray 120 is fabricated as a 10 micron $SiO_2$ coating layer 122 on 300 micron base layer 121 of Si. As the laser wavelength (illumination light 112) is tuned over the 80 nm range, the resulting reflectivity vs. wavelength curve 132 is characterized both a maximum and a minimum value (FIG. 5A). Small amounts of target molecule 24 binding to the microarray 120 will shift the wavelength of maximum and minimum reflectivity (FIG. 5A). The photodetector array 130 records these curves for each pixel as the wavelength is tuned, and a central processor (i.e., computer) compares how each pixel is shifted following a binding event. Since the refractive index of most biomaterial is close to that of glass (both low index around n=1.4), this binding can be modeled as a small increase in the glass layer thickness.

Figure 5B:
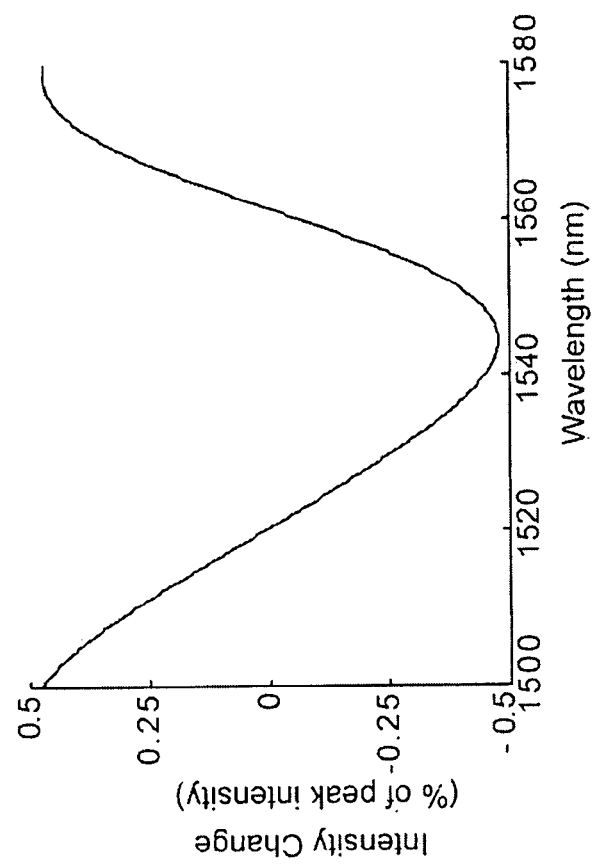
FIGS. 5A-B are examples of the data expected to be measured using a direct reflectivity methodology.
Figure 5A:
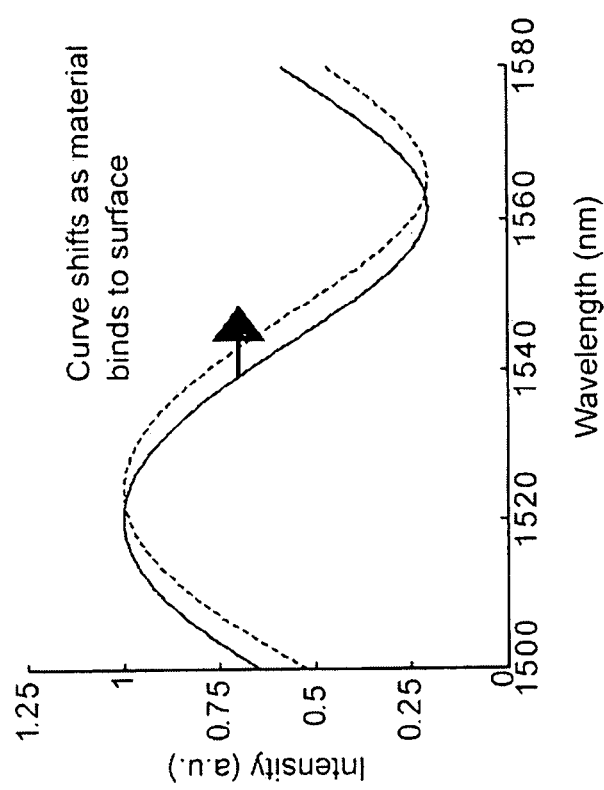

FIG. 5B shows the change in intensity due to a 1 nm increase in $SiO_2$ thickness as a percent of the peak intensity recorded. A 1 nm increase in $SiO_2$ thickness corresponds, for instance, to about a 50 $pg/mm^2$ layer streptavidin (50 kDa protein) binding to a microarray location 129. The percent change in intensity without using a layered substrate (relying only on increase absorption to affect the reflectivity) would be negligible and undetectable.

The $SiO_2$ on Si layered microarray 120 structure demonstrates the principle of (layered) substrate enhanced detection. More complicated layered structures may be used to further improve detection sensitivity. When choosing materials for the layered microarray 120 of this invention, it is important that the refractive index of the top layer be closely matched to the index of the target molecules 124 to be detected. $SiO_2$ works well for many biomolecules including, for example, DNA, RNA, and protein. Also, the addition of target molecules 124 (e.g., biomolecules) to the coating layer 122 significantly shifts the wavelength-reflectivity characteristic of the microarray 120 as a whole.

The direct reflectivity methodology combines the high throughput features of a microarray with high sensitivity of laser detection methods in a manner that can be configured to provide real-time binding information. Another advantage is that this can be accomplished using relatively inexpensive commercially available optical equipment including a gray scale camera and simple tunable laser. Alternative illumination sources 110 include, for example, a broad spectrum light source with a narrow tunable filter.

B. Split Beam Interferometry

Figure 6:
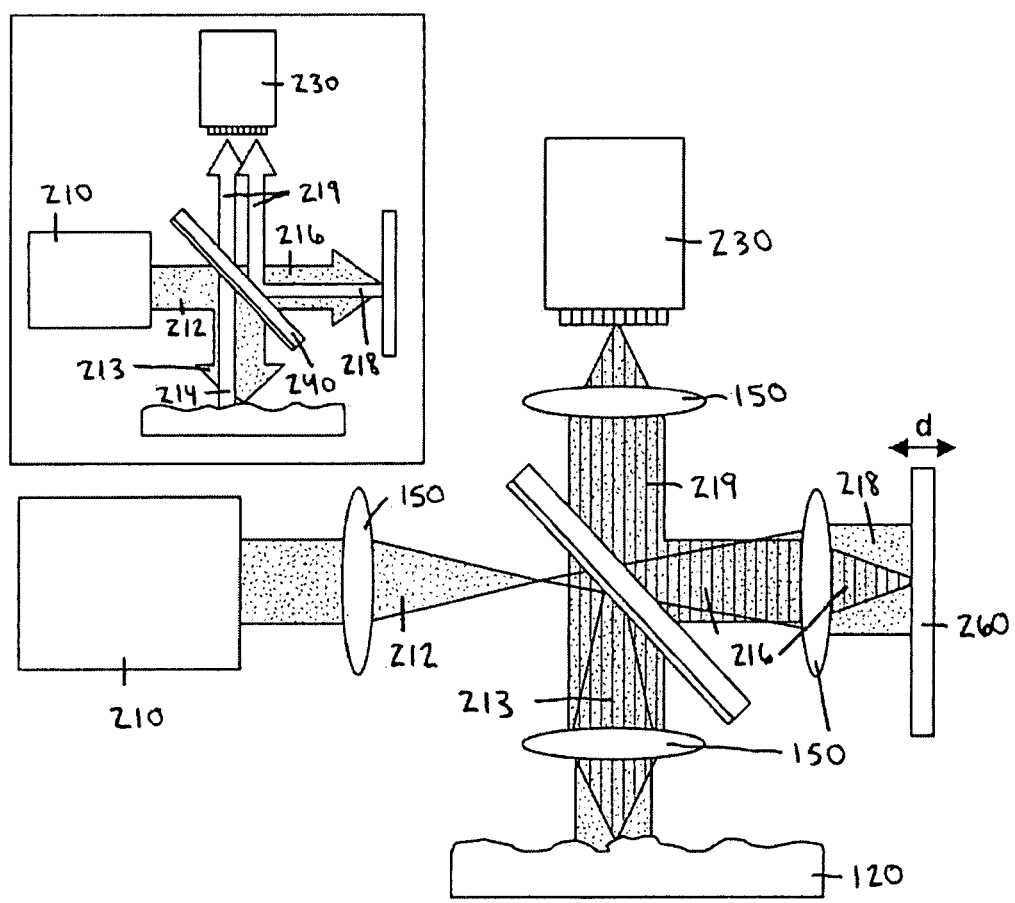
FIG. 6 is a schematic diagram of the split beam interferometry methodology; the inset is a simplified schematic showing the light paths.

The component set-up for split beam interferometry method is similar to the direct reflectivity method described above in that the microarray 120 is illuminated from above by an illumination light 212. In the split beam method, however, differs from the direct reflectivity method as shown by the schematic device 200 in FIG. 6. The illumination source 210, in this case, is preferably a single wavelength laser, but a broad spectrum light with a narrow band-pass filter may also be used. The illumination beam 212 is split by a beam splitter 240 into a sample illumination beam 213 and a reference illumination beam 216 which are directed onto the microarray 120 and the reference reflector 260, respectively. The sample illumination beam is reflected by the microarray 120 as the sample image light 214 and the reference illumination beam 216 is reflected by the reference reflector 260 as the reference image light 218. The sample image light 214 and the reference image light 218 are combined by the beam splitter 240 into the reflected beam 219 which is directed onto the photodetector 230. The reference image light 218 interferes with the sample image light 214 in the combined reflected beam 219. As detailed further below, it is the interference pattern that provides information about the apparent height of the microarray 120.

Figure 7B:
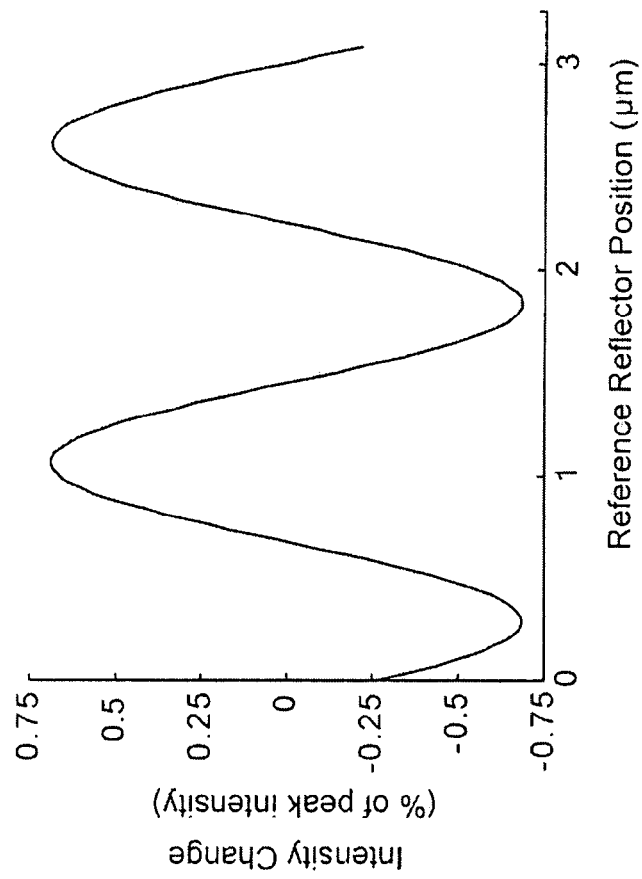
FIGS. 7A-B are examples of data expected to be measured using a split beam interferometry methodology.
Figure 7A:
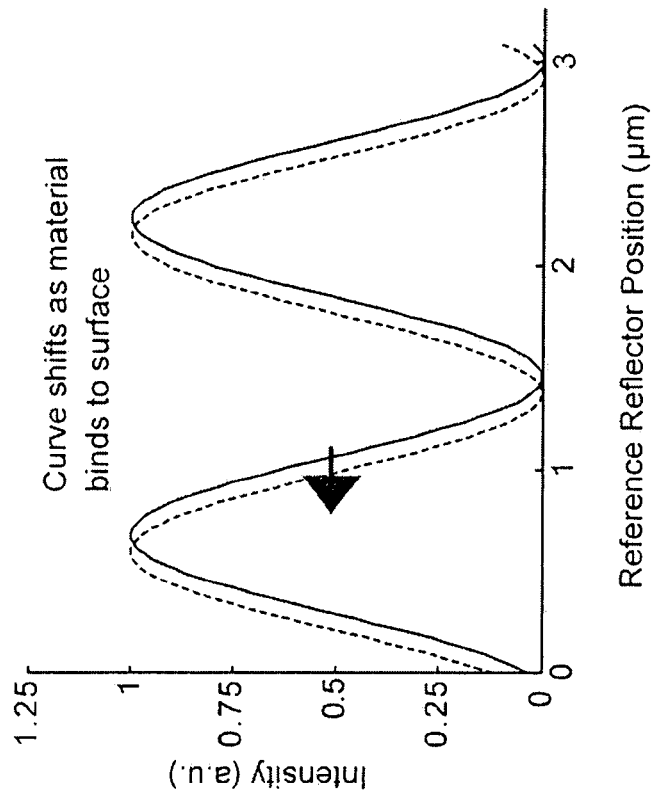

During operation, the position of the reference reflector 260 is swept, perpendicular to the reference illumination beam 216, by a distance "d". Interference between the reference image light 218 and the sample image light 214 changes as a function of the position of the reference reflector 260. As shown in FIGS. 7A-B, the photodetector 230 and associated central processor create curves of reflective intensity vs. reference mirror position for each pixel. The curve shifts as the apparent height of the microarray changes. The calculation and analysis methodology is the same as for PSI {supra}.

The standard split beam interferometry setup is capable of detecting microarray 120 surface heights with 1 nm accuracy or better for single layer, highly reflective surfaces. For low-index material such as $SiO_2$ and biomaterial, standard interferometry perform poorly as a result of the low surface reflectivity. One simple solution is to use an equally low reflectivity reference reflector 260 and turn up the source power to compensate for the loss. The results can be improved even further, however, by using a layered substrate as described for the microarrays useful in the standard illumination method. However, further modification of the layered substrate yields greater improvements. For split beam interferometry, a thinner coating layer 122 and a thicker base layer 121 are desirable. In one embodiment, the coating layer is 270 nm of $SiO_2$ (n=1.4) on a thicker piece of Si for use with an illumination beam 112 having a wavelength ($\lambda$) of 1550 nm. Thus, the coating layer 122 of $SiO_2$ has a thickness of $\lambda/4$ (i.e., "a quarter-wave layer"). At this thickness, reflectivity around 1550 nm is minimized. Sensitivity of the interference pattern in the combined reflected beam 219 to small changes in reference mirror position is, therefore, maximized. Table 1 shows the maximum change in intensity (as a percent of peak intensity) as a function of mirror position recorded during the data collection.

Again, a quarter-wave layer of $SiO_2$ on Si is only one example of a layered substrate useful with the split beam method. More complicated substrates may yield even greater sensitivities. The important feature of a desirable layered substrate is that the phase of the sample image light 214 change rapidly with the addition of biomaterial to top of the coating layer 122 of closely matched index.

Another example a useful layered substrate for use in microarrays is $SiO_2$ on gold. Gold is highly reflective and so a highly reflective gold reference mirror should be used as well. The reflectivity of the sample will remain high across different wavelengths, but the phase of the reflected light will change rapidly with the addition of a small amount of biomaterial when the apparent thickness of the $SiO_2$ layer is approximately an odd integral number of wavelengths.

C. Modified Split Beam Interferometiy

Figure 8B:
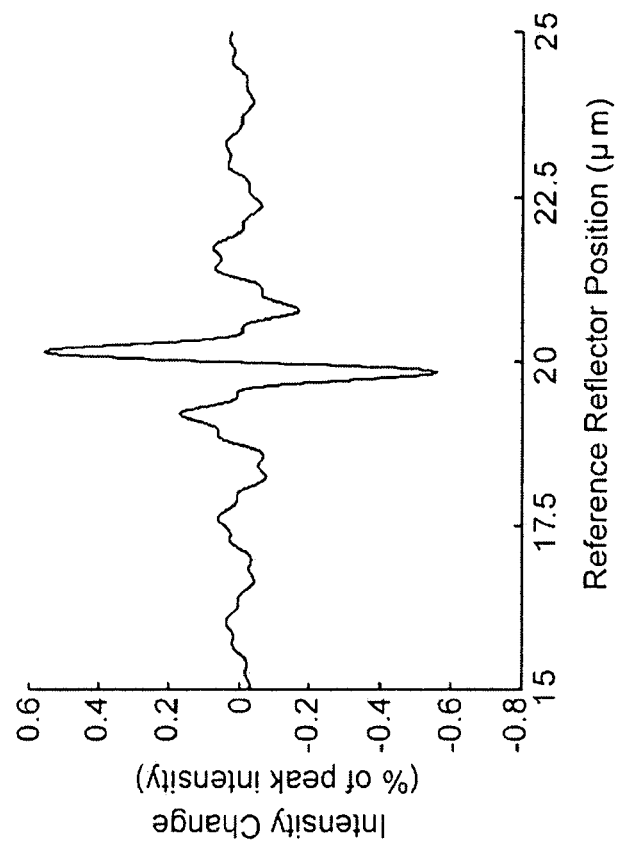
FIGS. 8A-B are examples of data expected to be measured using a modified split beam interferometry methodology.
Figure 8A:
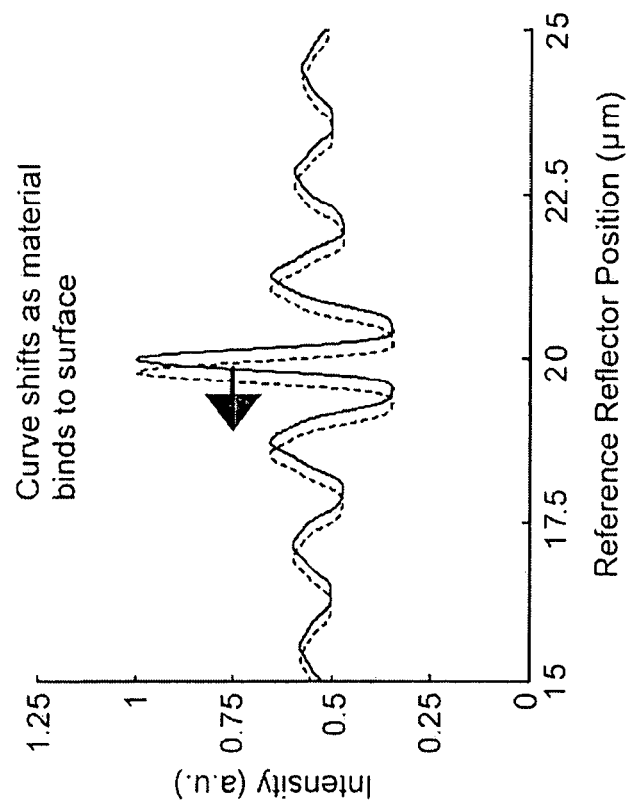
Figure 9:
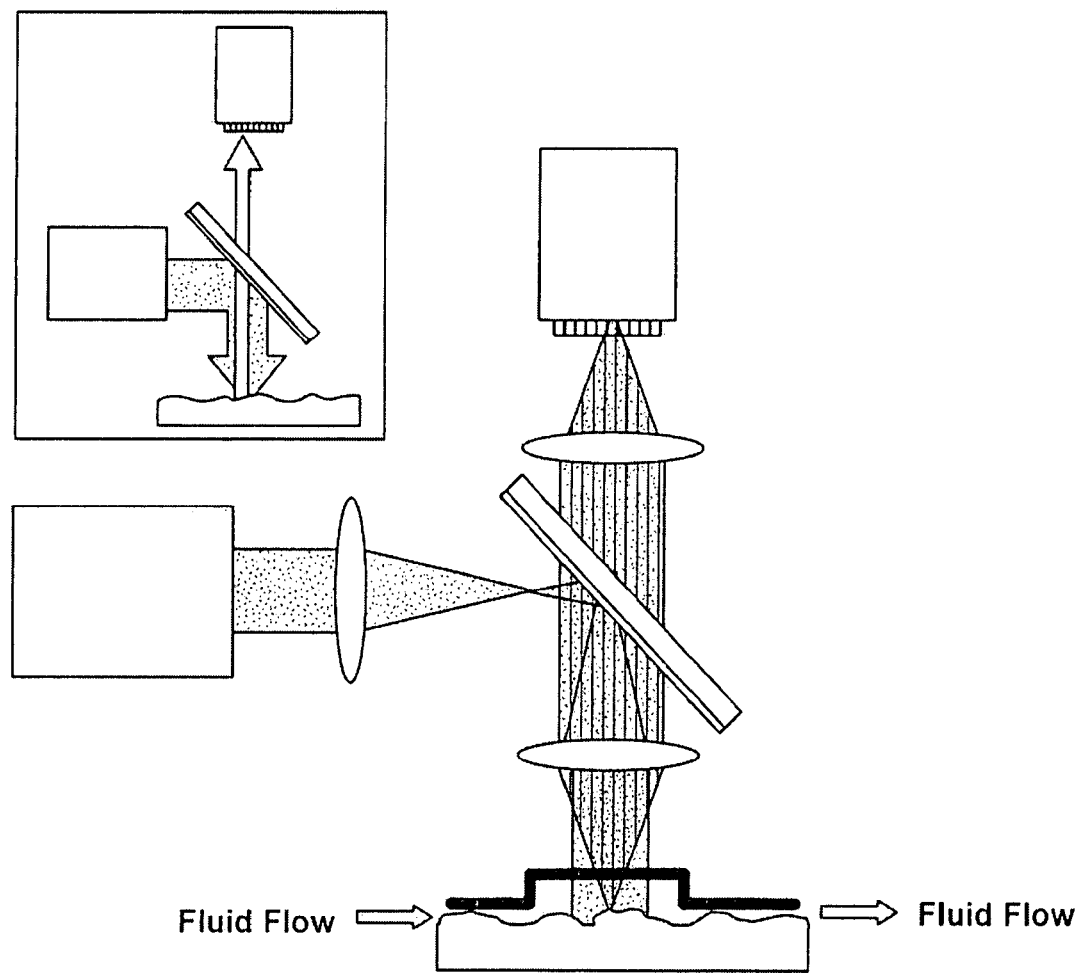
FIG. 9 is a schematic diagram of the direct reflectivity methodology and layered substrate adapted for use in a flow cell and configured to obtain real-time binding data.

The modified split beam interferometry set-up and methodology is very similar to the split beam method described above. The optical setup is the same as that shown in FIG. 6 for split beam interferometry. The difference is that the illumination source 210 is a white light source instead of a single wavelength laser. Again a reference reflector 260 is swept over a distance "d" with the difference being that interference using a white light source will only be observed when the reference reflector 260 is about the same distance from the photodetector 230 as the apparent surface of the microarray 120 (within the source coherence length). The intensity of the interference is recorded at each pixel and curves of intensity vs. reference reflector 260 position are again generated (FIGS. 8A-B). The reference reflector 260 position where interference is greatest indicates the apparent surface height at that location. This method is normally accurate down to the nanometer scale using a highly reflecting sample reference mirror. Similar accuracy is attainable using low reflectivity samples with a low reflectivity reference mirror and turning up the source power. Additional sensitivity enhancements are gained from the use of a layered substrate in the microarray. Table 1 shows the maximum change in intensity (as a percent of peak intensity) as a function of mirror position recorded during the data collection using the same 270 nm $SiO_2$ on Si substrate. The increased sensitivity is because the layered substrate causes a phase shift in the reflected light greater in some wavelength regions depending on the thicknesses of the layers chosen.

TABLE 1

Sensitivity Comparison of Layered Substrates Using Various Optical Detection Methodologies

| Detection Method* | Base Layer | Coating Layer | Material Sensed | Reference Reflector Material | Sensitivity 100*(Change in intensity) (Peak Intensity Recorded) |
|---|---|---|---|---|---|
| DRM | Thick $SiO_2$ | None | 1 nm $SiO_2$ | — | 0.00 |
| DRM | Thick Si | 10 μm $SiO_2$ | 1 nm $SiO_2$ | — | 0.47 |
| SBI | Thick $SiO_2$ | None | 1 nm $SiO_2$ | $SiO_2$ | 0.41 |
| SBI | Thick Si | 270 nm $SiO_2$ | 1 nm $SiO_2$ | $SiO_2$ | 0.73 |
| MSBI | Thick $SiO_2$ | None | 1 nm $SiO_2$ | $SiO_2$ | 0.32 |
| MSBI | Thick Si | 270 nm $SiO_2$ | 1 nm $SiO_2$ | $SiO_2$ | 0.65 |

*DRM = direct reflectivity method; SBI = split beam interferometry; MSBI = modified split beam inferometry.

D. Microarray Detection

Microarray technology, including methods for making microarrays, procedures for conducting microarray experiments, and applications are well known in the art [see, for example, Schena 2000]. The chemistry for the attachment of capture molecules to $SiO_2$ substrates (i.e., the coating layer) are also well known in the art. A significant advantage of the present invention over current microarray detection methodologies is that the present techniques eliminate the need to detectably label the target molecules prior to performing the binding reaction on the microarray. A second advantage of the present techniques described herein is that a baseline height scan of the microarray may be performed prior to running the binding reaction with the target molecules so that the height of each detection location may be compared before and after target molecule binding. This eliminates the need for height and/or density uniformity of the capture molecules across the entire microarray. It also serves to reduce interexperimental variability (e.g., that result from manufacturing defects) where replicate microarrays are compared.

An exemplary microarray useful in accordance with the principles of this disclosure may be created on the layered substrate by first cleaning the substrate surface with acetone, methanol, water, and $N_2$ gas, then etching the surface with 10% NaOH for about 10 minutes. The surface is next silanized and functionalized with an amino-silane (for instance: 3-aminopropyl-triethoxysilane). Capture DNA is then be spotted at spatially distinct locations on the surface using a hollow pin (usually done robotically), using standard ink-jet printing technology [Hughes 2001], or using standard photolithography techniques [Singh-Gasson 1999]. The DNA is cross-linked (covalently bonded) to the surface by irradiation with UV light. The surface is finally rinsed before use. Alternative methods exist for making arrays including methods that use photolithography.

The microarray is then scanned using any method in accordance with the principles of this invention to determine the initial height of each location. Next, target DNA is introduced to the surface via a solution, rinsed, and dried. The array is scanned again using the same method and the increase in height is recorded for each location. The change in height is an index of the amount of target DNA bound to that location.

E. Alternative Substrate Designs $SiO_2$ layered on Si, as described above, is the simple case of a layered substrate that can be used in accordance with the principles of this disclosure. More complex layered substrates may also be used. The most desirable property for layered substrates is that the beam reflected from the target molecule surface undergoes a maximum phase change for a small change in the amount of material bound. A layered substrate consisting of many semitransparent layers of different optical indices can exhibit a very rapid change in both the intensity and phase of the reflected light for a small amount change in wavelength. Similarly, such a structure may exhibit a very rapid change in phase for a small amount of material modifying the thickness of the top layer. For example, a stack consisting of 270 nm of $SiO_2$, 340 nm of Si, 270 nm of $SiO_2$, 340 nm of Si, and 270 nm of $SiO_2$ on an Si substrate has high reflectivity for wavelengths of 1550 nm. If the top $SiO_2$ layer is slightly modified with binding molecules, the reflectivity will remain high, but the phase will change rapidly. This rapid phase change will give an enhanced signal in either of the split beam interferometry methods described above.

The key is to create layered substrates that cause a rapid change in the phase of the reflecting light resulting from a small change in surface height. Materials may be used other than Si and $SiO_2$. Alternative coating layers that are useful in layered substrates include dielectric substances such as $Si_3N_4$.

Figure 12:
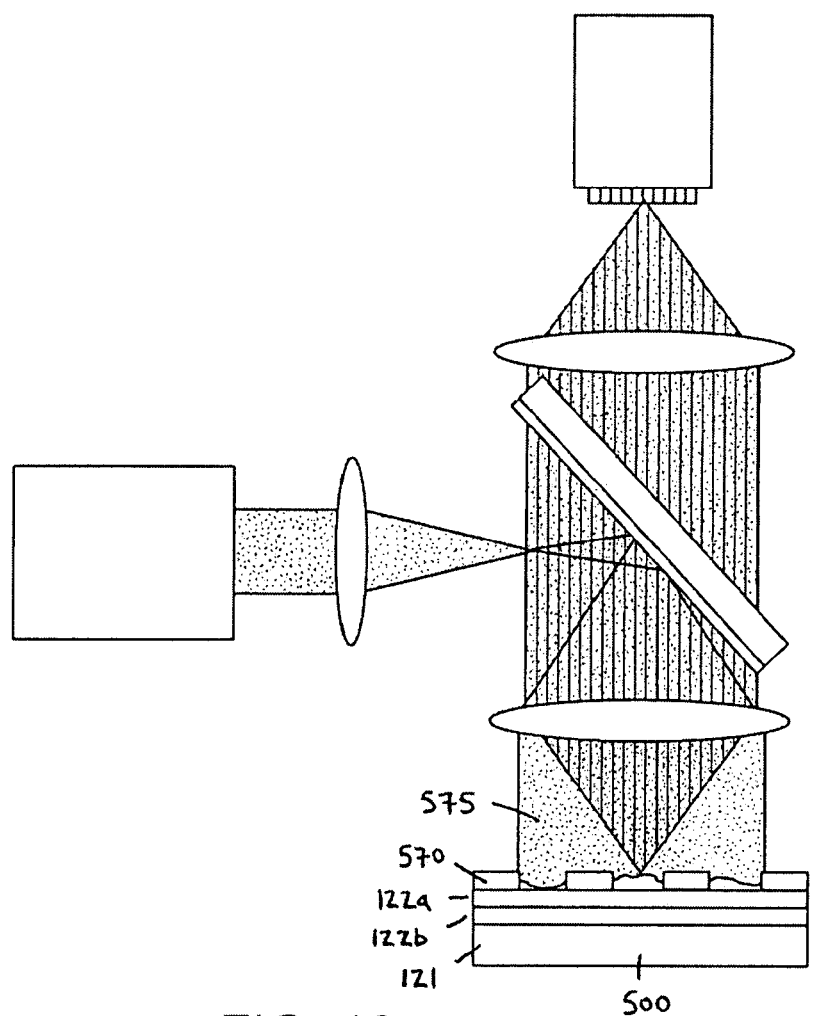
FIG. 12 is a schematic optical detection apparatus illustrating the use of a layered substrate containing reaction wells.

In addition to the standard substrate configurations such as surface coating with capture molecules, either as a film or in spatially discrete locations as a microarray, alternative configurations may be useful depending upon the application. For example, in one alternative embodiment, an additional discontinuous layer is formed on top of the coating layer such that individual reaction wells are created. These reaction wells are desirably about 200 μm×200 μm×1 mm, but any convenient size may be used, depending upon the specific application and reaction conditions. These reaction wells may serve to contain the bonding reaction that fixes the capture molecules to the substrate surface, or the wells may be used to contain individual binding reactions in spatially and/or chemically distinct environments. FIG. 12 illustrates a layered substrate 500 having a base layer 121, a top coating layer 122a and an intermediate coating layer 122b built in accordance with the principles of this disclosure. The layered substrate 500 further comprises reactions wells 575 formed by well walls 570. Each reaction well 575 may contain the same or different reactants (e.g., target molecules, capture molecules, biological/environmental samples), in a liquid medium, as the other reaction wells 575 on the same layered substrate 500. The reaction wells 575 may be formed by layering a polymeric (e.g., PDMS) or other coating material (e.g., $SiO_2$) on top of the top coating layer 122a. Alternatively, the reaction wells 575 may be formed by etching or soft lithography such that the wells are "cut" into the top coating layer 122a. For convenience, the layered substrate 500 is shown in conjunction with the direct reflectivity measurement apparatus, but these substrates are also useful with either the split beam interferometry or the modified split beam inferometry methodologies of this disclosure.

F. Real-Time Instrument Design

Figure 10:
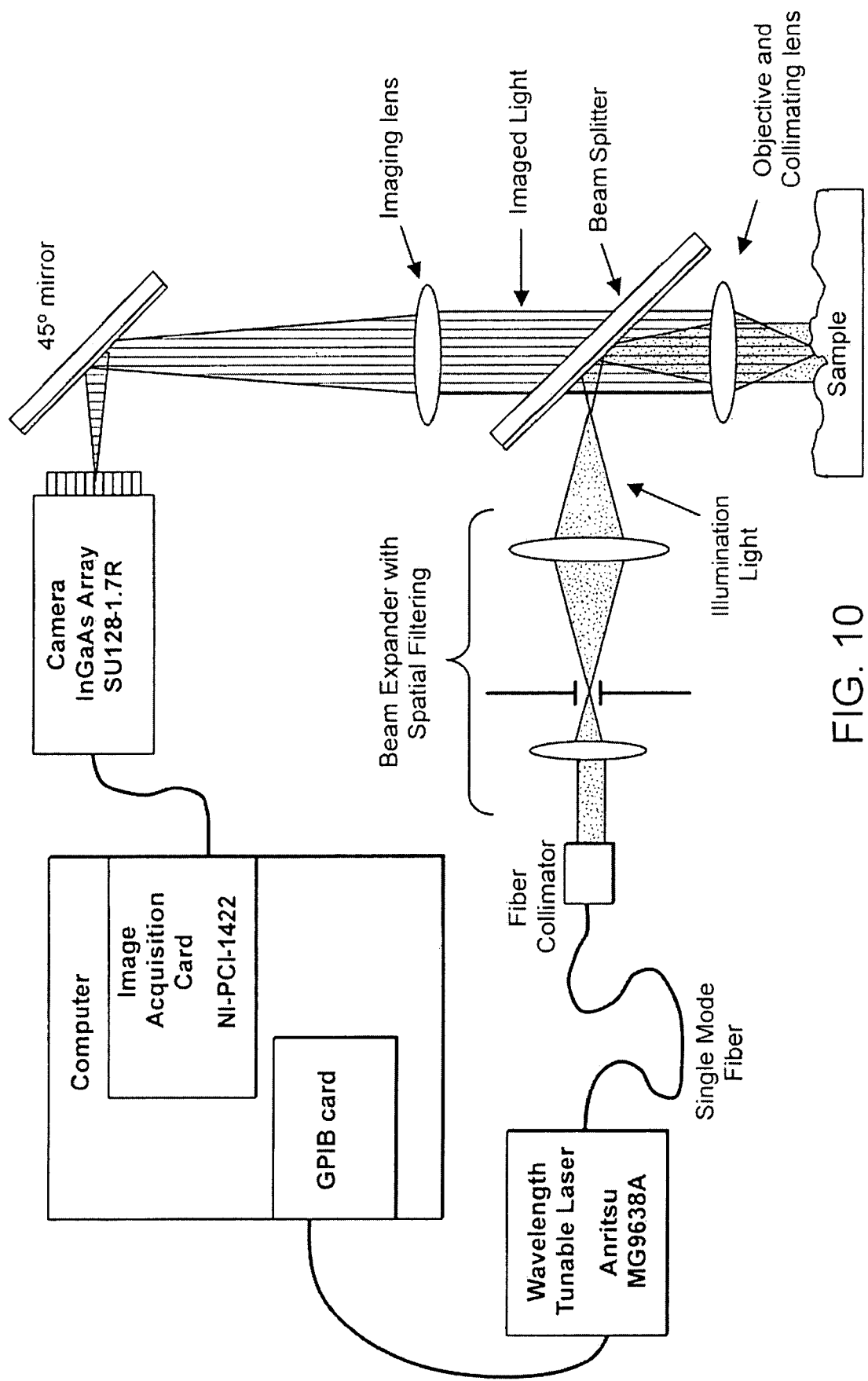
FIG. 10 is a schematic of the optical component set-up used in a proof-of-concept experiment for the direct reflectivity methodology.

In order to perform real-time measurements so that binding kinetics between the target and capture molecules may be calculated, the substrate or microarray is desirably incorporated into a flow cell. The flow cell should be at least semi-transparent and allow the delivery of target molecules to the capture molecules in an fluid environment. Suitable fluids include liquids (e.g., an aqueous solution) and gases (e.g., air or an inert gas). FIG. 10 is a schematic illustrating the manner in which a substrate 420 comprising capture molecules 123 (not shown) may be incorporated into a direct reflectivity device constructed in accordance with the principles of this disclosure. The flow cell 400 is easily adapted for the split beam methodologies. When used in a flow cell 400 configuration, the height measurements indicating binding are desirably be performed quickly and repeatedly to observe binding at various times during the pre-equilibrium state. This would enable the user to extract kinetics information about the rate of the binding reaction. If desired, the user may continue the measurements after binding equilibrium is reaching and change the fluid to one that lacks target molecules in order to measure off-rate kinetics. The user may also introduce heat, pH change, electric field, or other physical or chemical alterations to further investigate binding kinetics.

EXAMPLE 1

Direct Reflectivity Method

FIG. 10 is a schematic of the optical set-up used for the following experiments.

The illumination source was a tunable wavelength laser (Anritsu MG9638A) that can step light between 1500 nm and 1580 nm in picometer increments, and was controlled using a GPIB card and central processor. The power was kept at about 0.1 mW. SMF-28 fiber optic carries the light from the laser to the optical setup. The light exiting the fiber was collimated by an objective and then beam expanded with two additional lenses. There was an aperture in the beam expander to spatial filter and pass the lowest order Gaussian mode exiting the fiber. The light then reached a beam splitter that directed part of the light onto the sample. The light path was as follows: the light from the laser was directed by a beam splitter onto the sample; the light reflected from the sample and passed through the beam splitter, reaching the camera mounted above.

Imaging optics were included for imaging the sample surface onto the camera. An objective was placed above the sample and below the beam splitter. The light exiting the beam expander configuration was converging such that the objective lens re-collimated it when it passes through to the sample. Alternatively, the beam splitter may be placed close to the sample and the objective above it. In this case, the beam expander would produce a collimated beam. The illumination light that reaches the sample in either case is collimated and the reflected light is imaged. The lenses and beam splitter were AR coated for 1550 nm to avoid unwanted cavity effects that would produce a wavelength dependency.

The camera used an InGaAs array (SU 128-1.7R; Sensors Unlimited). Lab View software was used to control the laser and capture images from the camera. An NI-1422 frame grabber card (National Instruments) was used to capture the images.

A layered substrate "test sample" was prepared by oxidizing 5 microns of $SiO_2$ on a 500 micron thick Si wafer piece. To mimic biomaterial binding to the surface, 10 nm×100 micron strips of $SiO_2$ were patterned on the substrate surface. The index of $SiO_2$ is about n=1.4 which is very similar to the index of DNA and many proteins.

The illumination light wavelength was stepped from 1500 nm to 1580 nm in 0.2 nm increments and an image was recorded at each step. First, a dark frame is captured with the lens cap on the camera. This dark frame was subtracted from all future measurements taken by the camera. A reference sample was used to characterize any wavelength dependence of the system. Then, the reference sample was replaced with the "test sample" and the measurement procedure was repeated.

The intensity vs. wavelength curve for each pixel was obtained and divided by the characteristic determined by the reference scan. The resulting curves were fit in a least squares sense to a model similar to the Matlab code entitled Method A included in the software package (Mathworks, Inc., Ver. 7.0.1). This curve-fitting model is based on the scattering matrix method for determining the reflectivity of thin films as described in chapter 5 of "Optical Waves in Layers Media" [Yeh 1988]. Alternatively, the curves may be fit to a simple sine wave as an approximation of the true reflectivity vs. wavelength curve. Another alternative is to take the Fourier transform of a collected curve and observe a phase increase which indicates a shift in the curve which indicates a change in surface height. However, results using the scattering matrix model are most accurate because the model accounts for multiple reflections within the semitransparent layer. The scattering matrix method works equally well for calculating the multiple reflections in more complicated structures with more layers.

Figure 11A:
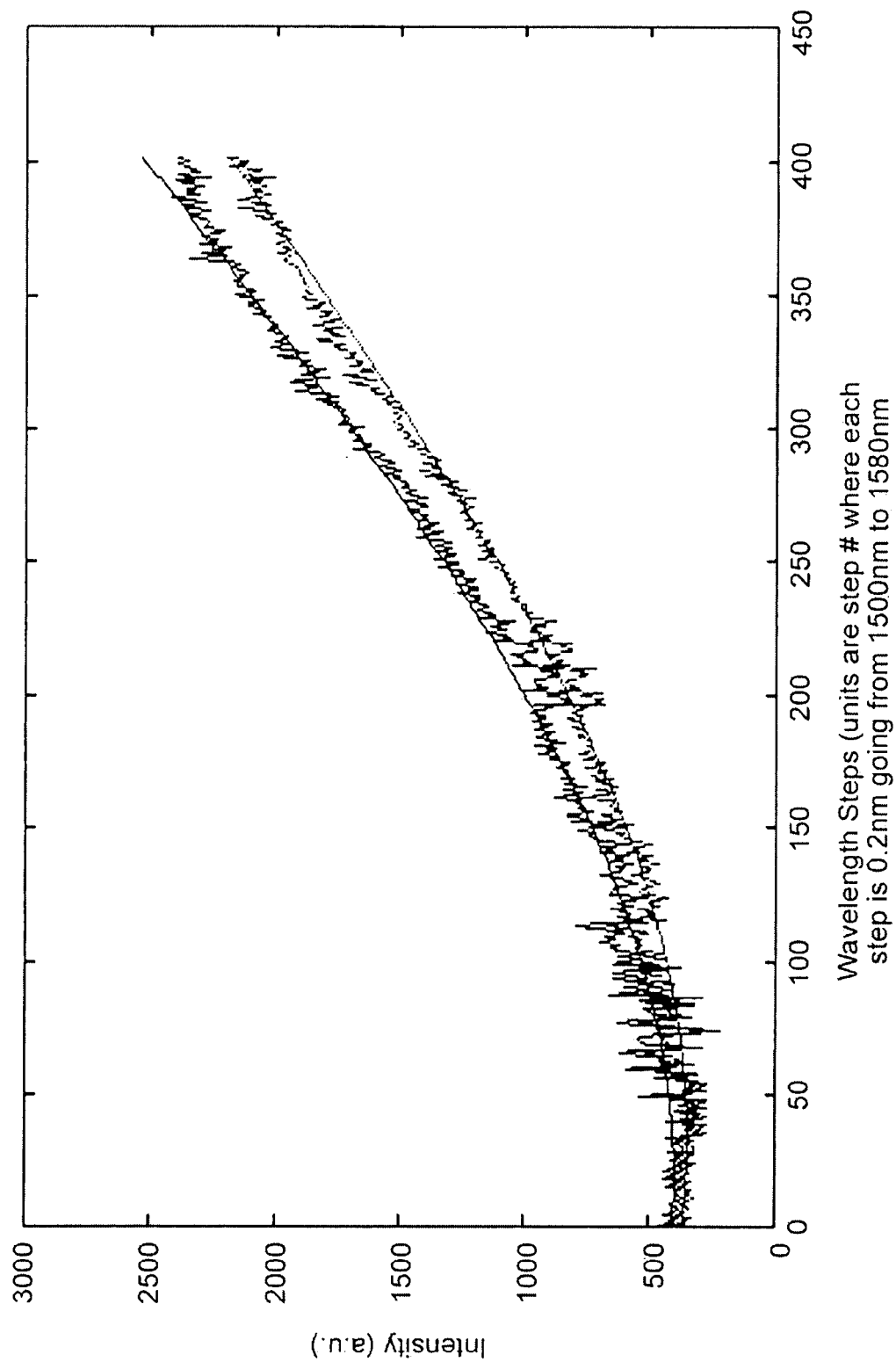
FIGS. 11A-C show the data obtained from a proof-of-concept experiment for the direct reflectivity methodology.
Figure 11B:
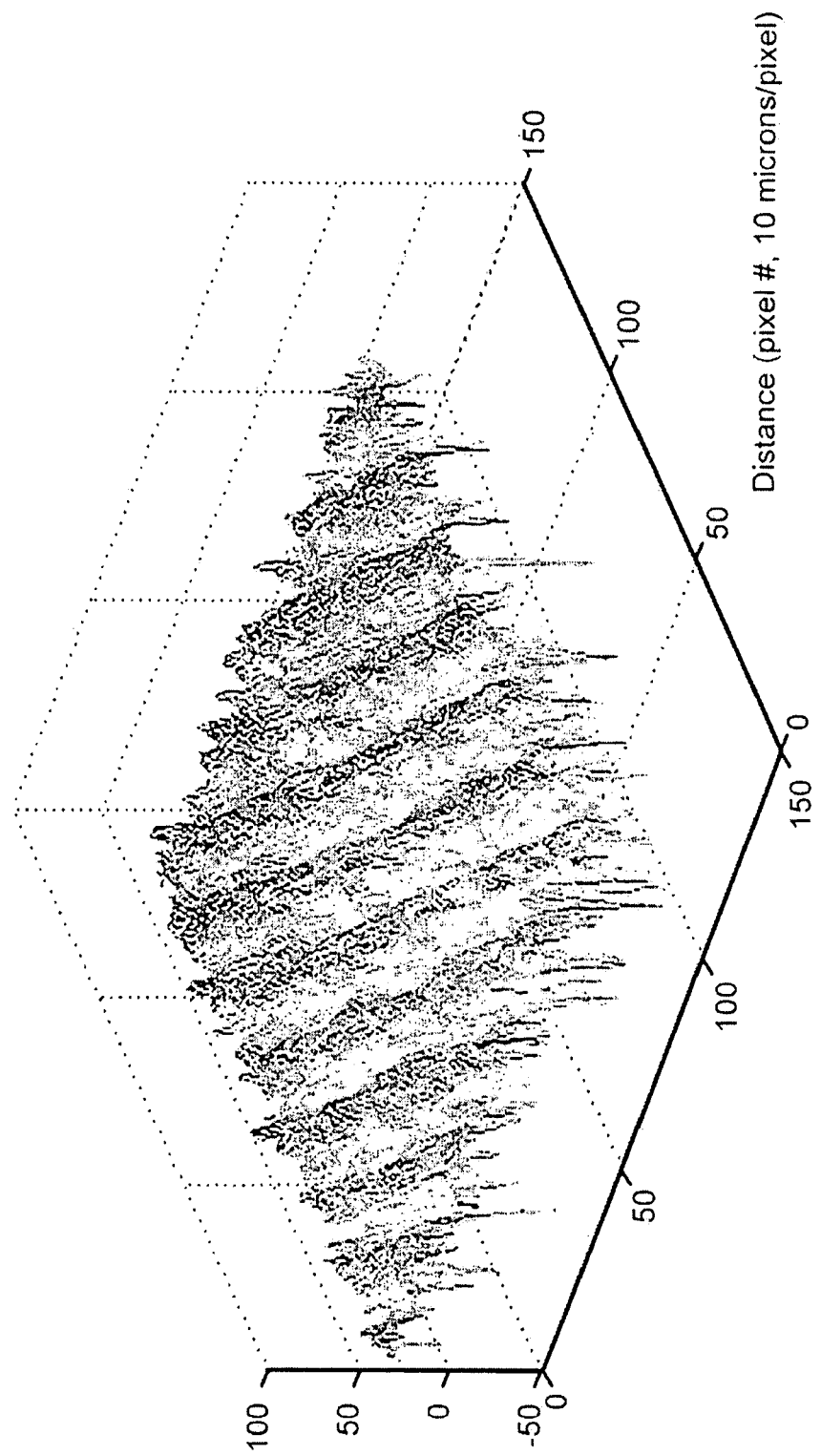
Figure 11C:
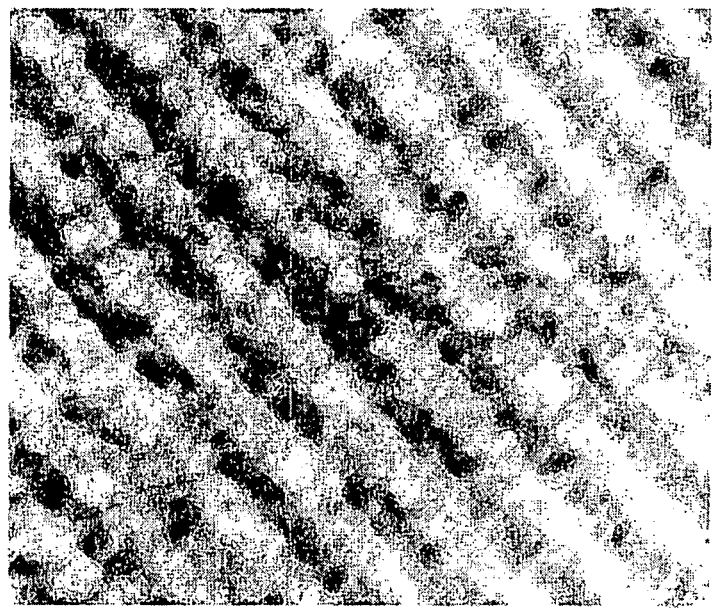

FIGS. 11A-C provide the results of this experiment. The relative layer thickness across the sample surface gives the change in height across the surface may be plotted as a 3D mesh or as a 2D image where the intensity of each pixel indicates its height. FIG. 11A is a graph of wavelength vs. intensity for two different pixels. The actual data and the fitted curve are shown. The lower curve represents a pixel corresponding to a location that has a greater height than the location corresponding to the upper curve. FIG. 11B is a 3D mesh graph showing the height measured at each pixel. FIG. 11C is a 2D image showing the intensity at each pixel in the image which represents the calculated height at the corresponding location.

This experiment has been successfully repeated with a visible CCD camera (Rolera from QImaging) and a tunable laser (New Focus Velocity) with a center wavelength of about 770 nm. Measurements of the 10 nm high strips were repeated with better than 1 nm repeatability.

REFERENCES (1) Brockman, et al. (2000). Surface Plasmon Resonance Imaging Measurements of Ultrathin Organic Films. Annu. Rev. Phys. Chem. 51, pp. 41-63.
(2) Hughes, T. R., et al. (2001). Expression profiling using microarrays fabricated by an ink-jet oligonucleotide synthesizer. Nature Biotechnology 19, pp. 342-7.
(3) Jenison, et al. (2001). Interference-based detection of nucleic acid targets on optically coated silicon. Nature Biotechnology, Vol. 19 pp. 62-65.
(4) Lin, et al. (2002). A label-free optical technique for detecting small molecule interactions. Biosensors & Bioelectronics 17, pp. 827-834.
(5) Lukosz (1991). Principles and sensitivities of integrated optical and surface plasmon sensors for direct affinity sensing and immunosensing. Biosensors & Bioelectronics 6, pp. 215-225.

(6) Moiseev, et al. (2004). Spectral Self Interference Fluorescence Microscopy. J. Appl. Phys, Vol. 96, No. 7.
(7) Moiseev, et al. (2006). DNA conformation on surfaces measured by fluorescence self-inteference. PNAS Feb. 21, 2006. Vol. 103, No. 8, pp. 2623-2628.
(8) Piehler, et al. (1996). Affinity Detection of Low Molecular Weight Analytes. Anal. Chem. 68, pp. 139-143.
(9) Schena (2000). Microarray Biochip Technology. Eaton. 2000. ISBN: 1-881299-37-6.
(10) Singh-Gasson S, et al. (1999). Maskless fabrication of light-directed oligonucleotide microarrays using a digital micromirror array. Nature Biotechnology 17 No. 10, pp. 974-978.
(11) Unlu, et al. (2004). Spectroscopy of Fluorescence for Vertical Sectioning. United States Patent Publication 2004/0036884.
(12) Unlu, et al. Resonant Cavity Imaging Biosensor. PCT/US2004/008558.
(13) Yeh (1988). Optical Waves in Layered Media. Wiley. ISBN: 0471828661.
(14) Zhang, et al. (2004). Micromechanical measurement of membrane receptor binding for label-free drug discovery. Biosensors and Bioelectronics. 19, pp. 1473-1478.

Other Embodiments

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An optical detection apparatus comprising:
(i) a reflective substrate having an uppermost surface, the reflective substrate comprising capture molecules adsorbed or covalently bound to the uppermost surface;
(ii) a tunable light source positioned above the reflective substrate, the tunable light source comprising an illumination beam having a tuning range of light comprising varying wavelengths, the illumination beam being directed substantially perpendicular to the uppermost surface of the substrate; and
(iii) a photodetector array operably linked to a central processor configured to measure an intensity of light reflected from the substrate.

2. The apparatus of claim 1, wherein the light source is selected from the group consisting of a tunable laser and a broad spectrum light source operably linked to a tunable filter.

3. The apparatus of claim 1, wherein the substrate is a layered substrate comprising a base layer, at least one coating layer having a refractive index different from the refractive index of the base layer, and a plurality of spatially distinct binding locations, wherein each of the binding locations comprises capture molecules bound to the topmost coating layer.

4. The apparatus of claim 1, wherein the photodetector array is selected from the group consisting of a CCD camera and an InGaAs array.

5. The apparatus of claim 1, wherein the light source is tunable over a wavelength range of at least 5 nm.

6. The apparatus of claim 1, wherein the light source is tunable within a wavelength range comprising about 1450 nm to about 1650 nm.

7. The apparatus of claim 1, wherein the central processor is capable of calculating reflectivity curves of illumination intensity as a function of illumination wavelength for substantially every pixel of the photodetector array.

8. An optical detection apparatus comprising:
(i) a reflective substrate having an uppermost surface, the reflective substrate comprising capture molecules adsorbed or covalently bound to the uppermost surface;
(ii) a tunable light source positioned above the reflective substrate, the tunable light source comprising an illumination beam having a tuning range of light comprising varying wavelengths, the illumination beam being directed substantially perpendicular to the uppermost surface of the substrate;
(iii) a movable reference reflector having substantially the same refractive index as the reflective substrate;
(iv) a first beam splitter capable of splitting the illumination beam into a sample illumination beam and a reference illumination beam, the beam splitter further capable of directing the sample illumination beam onto a reflective substrate and directing the reference illumination beam onto a reference reflector;
(v) a second beam splitter capable of combining the light reflected from the reflective substrate with the light reflected from the reference reflector into an imaged light beam;
and
(vi) a photodetector array positioned to measure the intensity of the imaged light beam operably linked to a central processor configured to capture images produced by the photodetector array.

9. The apparatus of claim 8, wherein the illumination beam is substantially a single wavelength.

10. The apparatus of claim 8, wherein the light source is selected from the group consisting of a tunable laser and a broad spectrum light source operably linked to a tunable filter.

11. The apparatus of claim 8, wherein the illumination beam comprises multiple wavelengths.

12. The apparatus of claim 11, wherein the illumination beam is white light.

13. The apparatus of claim 8, wherein the substrate is a layered substrate comprising a base layer, at least one coating layer having a refractive index different from the refractive index of the base layer, and a plurality of spatially distinct binding locations, wherein each of the binding locations comprises capture molecules bound to the topmost coating layer.

14. The apparatus of claim 8, wherein the photodetector array is selected from the group consisting of a CCD camera and an InGaAs array.

15. The apparatus of claim 8, wherein the illumination beam has a wavelength of between about 1450 nm to about 1650 nm.

16. The apparatus of claim 8, wherein the central processor is capable of calculating reflectivity curves of illumination intensity as a function of a displacement position of the reference reflector for substantially every pixel of the photodetector array.

* * * * *